United States Patent
Pillalamarri et al.

(10) Patent No.: US 10,658,084 B2
(45) Date of Patent: *May 19, 2020

(54) BASAL INSULIN MANAGEMENT

(71) Applicant: Insulet Corporation, Acton, MA (US)

(72) Inventors: Sandhya Pillalamarri, Methuen, MA (US); Jorge Borges, Billerica, MA (US); Susan Mercer, Waltham, MA (US)

(73) Assignee: Insulet Corporation, Acton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/545,136

(22) Filed: Aug. 20, 2019

(65) Prior Publication Data

US 2019/0371461 A1 Dec. 5, 2019

Related U.S. Application Data

(63) Continuation of application No. 15/811,120, filed on Nov. 13, 2017, now Pat. No. 10,438,698.

(60) Provisional application No. 62/422,281, filed on Nov. 15, 2016.

(51) Int. Cl.
*G06F 19/00* (2018.01)
*G16H 40/63* (2018.01)
*G16H 20/17* (2018.01)
*G16H 40/67* (2018.01)
*A61M 5/172* (2006.01)
*A61M 5/142* (2006.01)

(52) U.S. Cl.
CPC ............ *G16H 40/63* (2018.01); *A61M 5/172* (2013.01); *G06F 19/3468* (2013.01); *G16H 20/17* (2018.01); *G16H 40/67* (2018.01); *A61M 2005/14208* (2013.01); *A61M 2005/14292* (2013.01)

(58) Field of Classification Search
CPC .................. G16H 40/63; A61M 5/172; A61M 2005/14208; A61M 2005/14292
USPC ........................................................ 715/700
See application file for complete search history.

(56) References Cited

U.S. PATENT DOCUMENTS

2010/0017141 A1* 1/2010 Campbell ......... A61M 5/14244 702/19
2010/0064243 A1* 3/2010 Buck ................ A61M 5/14244 715/773

(Continued)

*Primary Examiner* — Jacinta M Crawford

(57) ABSTRACT

An improved basal insulin management system and an improved user interface for use therewith are provided. User interfaces are provided that dynamically display basal rate information and corresponding time segment information for a basal insulin program in a graphical format. The graphical presentation of the basal insulin program as it is being built by a user and the graphical presentation of a completed basal insulin program provides insulin management information to the user in a more intuitive and useful format. User interfaces further enable a user to make temporary adjustments to a predefined basal insulin program with the adjustments presented graphically to improve the user's understanding of the changes. As a result of being provided with the user interfaces described herein, users are less likely to make mistakes and are more likely to adjust basal rates more frequently, thereby contributing to better blood glucose control and improved health outcomes.

20 Claims, 18 Drawing Sheets

(56) References Cited

U.S. PATENT DOCUMENTS

| | | | |
|---|---|---|---|
| 2010/0077198 A1* | 3/2010 | Buck | G06F 19/3468 713/100 |
| 2010/0185183 A1* | 7/2010 | Alme | A61M 5/14276 604/891.1 |
| 2014/0032549 A1* | 1/2014 | McDaniel | G16H 40/63 707/736 |

* cited by examiner

FIG. 14

BASAL INSULIN MANAGEMENT

CROSS-REFERENCE TO RELATED APPLICATIONS

This application is a Continuation of U.S. application Ser. No. 15/811,120 filed Nov. 13, 2017, which claims the benefit of U.S. Provisional Application No. 62/422,281, filed Nov. 15, 2016, which are incorporated herein by reference in their entirety.

TECHNICAL FIELD

Embodiments generally relate to management of drug delivery. More particularly, embodiments relate to systems providing a user interface for building, implementing, and adjusting a basal insulin program.

BACKGROUND

Conventional basal insulin management systems require a user to manually enter start times, end times, and basal rates for each time segment of a basal program in a tabular format. Once data for each time segment is entered, these conventional systems display the basal program built by the user in a time-based tabular format. Users are typically overwhelmed with the time-based tabular format of the presented data. As a result, users often make mistakes when entering data or may be less likely to make adjustments to the basal program when doing so would be beneficial, thereby reducing the effectiveness of the diabetes management system.

Accordingly, what is needed is a basal insulin management system that presents information related to a basal insulin program in a more effective and intuitive manner, thereby increasing the effectiveness of the basal insulin management system.

BRIEF DESCRIPTION OF THE DRAWINGS

FIG. 14 illustrates an exemplary dynamic keyboard user interface provided by the portable electronic device of FIG. 1.

DETAILED DESCRIPTION

This disclosure presents various systems, components, and methods related to a basal insulin management system and a user interface provided by the basal insulin management system. Each of the systems, components, and methods disclosed herein provides one or more advantages over conventional systems, components, and methods.

Various embodiments provide an improved basal insulin management system and an improved user interface for interacting with the basal insulin management system. In various embodiments, user interfaces are provided that dynamically display basal rate information and corresponding time segment information for a basal insulin program in a graphical format. The graphical presentation of the basal insulin program as it is being built by a user and the graphical presentation of a completed basal insulin program provides insulin management information to the user in a more intuitive and useful format. Various embodiments further provide user interfaces enabling a user to make temporary adjustments to a predefined basal insulin program with the adjustments presented graphically to improve the user's understanding of the changes. As a result of being provided with the user interfaces described herein, users are less likely to make mistakes and are more likely to adjust basal rates more frequently, thereby contributing to better blood glucose control and improved health outcomes.

Figure 1A:
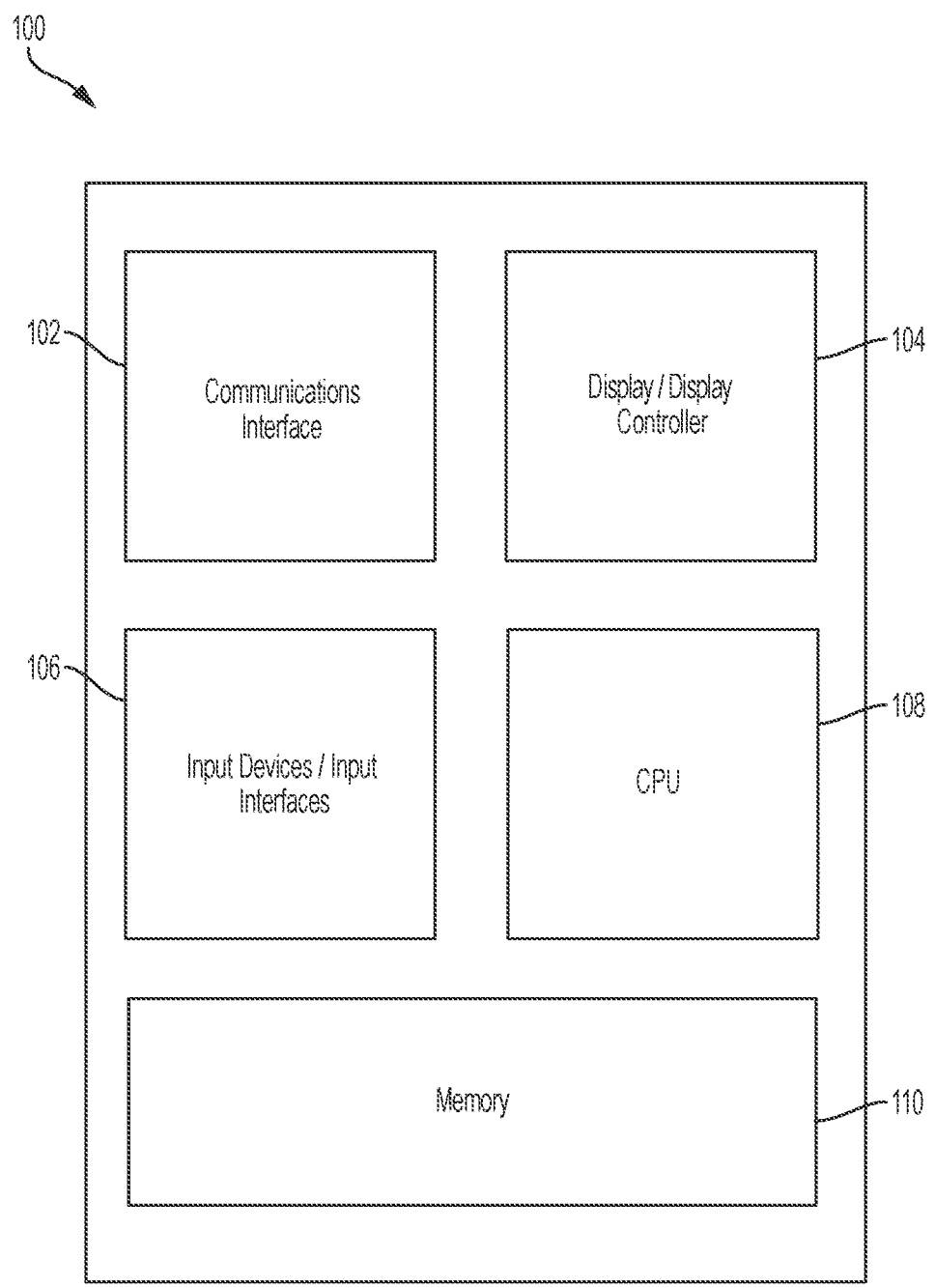
FIG. 1A illustrates an exemplary block diagram of a portable electronic device.

FIG. 1A illustrates an exemplary block diagram of a portable electronic device 100. The portable electronic device 100 can be, for example, a cellphone, a smartphone, a laptop, a tablet, or any other handheld and/or portable electronic computing device. The portable electronic device 100 can include a number of components as shown in FIG. 1A. Specifically, the portable electronic device 100 can include a communications interface 102, a display and a display controller 104, input devices and input device interfaces 106, a central processing unit (CPU) or a processor 108, and a memory 110.

The communications interface 102 can facilitate communication between the portable electronic device 100 and a number of remote devices (not depicted in FIG. 1A). The communications interface 102 can provide communications over wired or wireless links or interfaces according to any known wired or wireless communication standard or protocol. For example, the communications interface 102 can enable the portable electronic device 100 to communicate with one or more remote devices using, for example, Wi-Fi, a cellular communications standard, or Bluetooth.

The display and display controller 104 can represent a visual display that can render visual information and a display controller for controlling the rendering of any visual information. The visual information can be any graphical or textual information. The display 104 can be a touchscreen or a touch-sensitive display.

The input devices and input device interfaces 106 can represent any number of input devices and interfaces that can process any inputs provided through an input device. For example, the input devices 106 can include a mouse, a keyboard, a touchscreen, and/or a microphone. The input device interfaces 106 can include one or more receivers for receiving input signals from any corresponding input device.

The CPU or processor 108 can be a processor for executing instructions stored in the memory 110. The processor 108 can control and direct operation of any of the components of the portable electronic device 100. In particular, the processor 108 can control the operation or functionality of the communications interface 102, the display/display controller 104, and the input devices/input device interfaces 106.

The communications interface 102, the display/display controller 104, and the input devices/input device interfaces 106 can be implemented in hardware, software, or any combination thereof. The portable electronic device 100 can include other modules, components, or devices implemented in hardware, software, or any combination thereof and not shown in FIG. 1A to facilitate communication with remote devices, the receiving of input signals from a user, and the presentation of visual information to the user.

The portable electronic device 100 can operate with or as part of a diabetes management system (or other user monitoring and drug delivery system). For example, the portable electronic device 100 can operate with or as part of a diabetes management system that can control the delivery of insulin to a user. The portable electronic device 100 can be coupled to an insulin pump. For example, the portable electronic device 100 can be coupled to a drug delivery device such as the OmniPod® (Insulet Corporation, Billerica, Mass.) insulin delivery device and/or a drug delivery device such as those described in U.S. Pat. No. 7,303,549, 7,137,964, or 6,740,059, each of which is incorporated herein by reference in its entirety.

The portable electronic device 100 can further be coupled to any number of additional devices or components such as a glucose meter, remote sensors, and remote computing devices or servers. The processor 108 can execute instructions stored in the memory 110 to implement a diabetes management system—for example, to direct a drug delivery device to deliver a determined amount of insulin to a user based on one or more sensor inputs (e.g., data from a glucose monitoring device) and/or user inputs.

The portable electronic device 100 can provide a user interface to a user—for example, as part of a diabetes management system. The provided user interface can be used to control and monitor operation of the diabetes management system—such as controlling or monitoring delivery of insulin to a user over time.

The user interface can be provided by one or more of the components depicted in FIG. 1A. The user interface can be provided based on input signals received from communications interface 102 and input devices/input interfaces 106. The display/display controller 104 can present the user interface visually and can modify the user interface based on such received input signals. Further, the display/display controller 104 can retrieve data—such as graphics, icons, and text—from the memory 110 for display on the user interface based on the received input signals.

Each of the constituent components of the portable electronic device 100 can operate based on direction provided by the processor 108 in order to provide the user interface. For example, the user interface may include different operational modes. When a different mode is selected, the display/display controller 104 can retrieve different graphics from the memory 110 for presentation on the display 104. The different mode can be selected by the user through the touchscreen display 104 for example. Further, data received from a remote device by way of the communications interface 102 can also be presented on the user interface. Exemplary features of the user interface provided by the portable electronic device 100 are described in more detail herein.

Figure 1B:
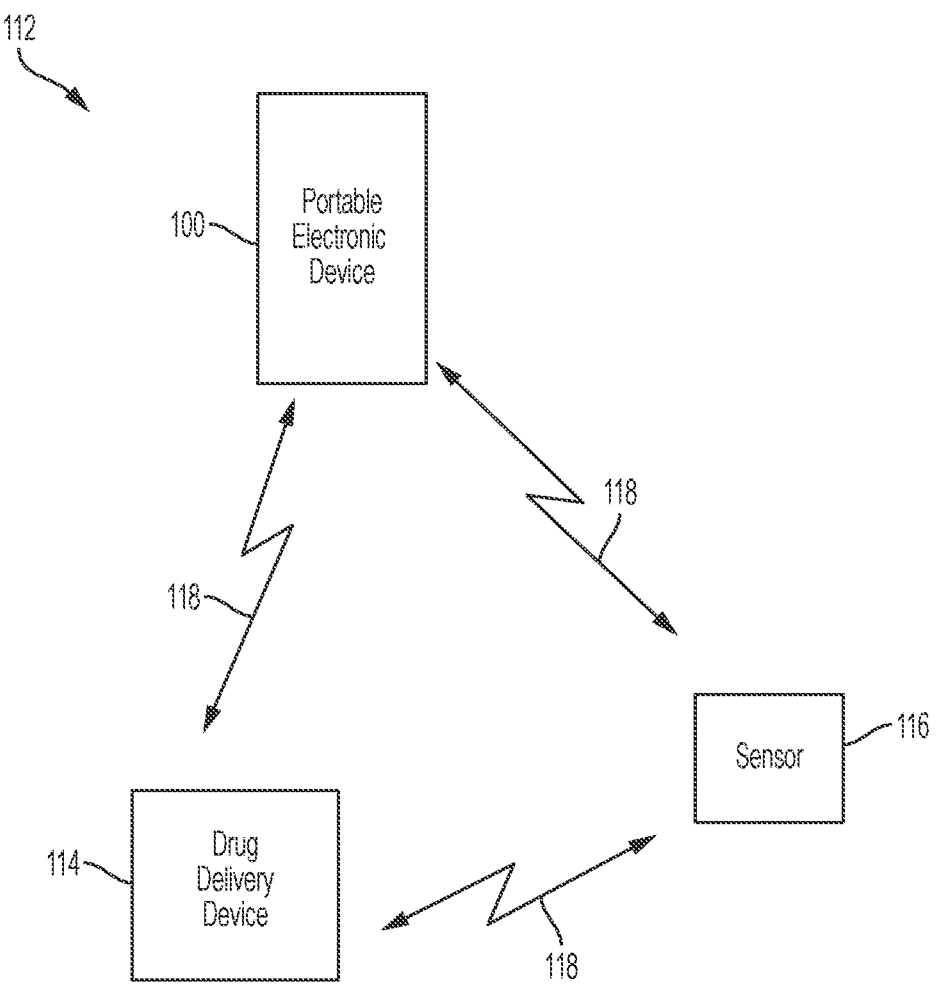
FIG. 1B illustrates an exemplary block diagram of a drug delivery system.

FIG. 1B illustrates an exemplary drug delivery system 112. The drug delivery system 112 can represent the drug delivery systems described herein. The drug delivery system 112 can include the portable electronic device 100. The drug delivery system 112 can further include a drug delivery device 114 and a sensor 116. The drug delivery device 114 can represent the drug delivery devices described herein. The drug delivery device 114 can administer any drug or therapeutic agent to a user. The sensor 116 can detect one or more physical, biological, and/or medical conditions of the user and can represent any of the sensors described herein. In various embodiments, the drug delivery device 114 can be an insulin drug pump (such as the insulin drug pump described herein) and the sensor 116 can be a glucose monitor. Generally, the drug delivery device 114 and the sensor 116 are worn on the body of the user. In various embodiments, the drug delivery device 114 and the sensor 116 can be combined into a single device.

As shown in FIG. 1B, the portable electronic device 100, the drug delivery device 114, and the sensor 116 can communicate over communications links 118. The communication links 118 can be wired or wireless communication links that operate according to any known wired or wireless communication protocol or standard such as, for example, Wi-Fi, a cellular communications standard, or Bluetooth. The communication links 118 can provide bidirectional communication between each of the components of the drug delivery system 112 such that any data or information can be shared between the portable electronic device 100, the drug delivery device 114, and the sensor 116.

In various embodiments, the drug delivery device 114 can deliver an amount of insulin to the user based on control or input provided by the portable electronic device 100. The control of the drug delivery device 114 can be based on information provided by the sensor 116. For example, glucose measurements of the user can be determined by the sensor 116 and shared with the portable electronic device 100. The user, by interacting with the user interface provided by the portable electronic device 100, can monitor, adjust, or otherwise control the delivery of insulin by the drug delivery device 112. The user interface provided by the portable electronic device 100 can allow the user to adjust basal delivery of insulin to the user and can be used to initiate bolus deliveries of insulin. In various embodiments, the user interface provided by the portable electronic device 100 enables the user to specify basal delivery and to direct the drug delivery device 114 to provide insulin to the user in accordance with the basal delivery specified by the user as described further herein.

Real-Time Basal Programming Graph

Many insulin pumps that operate as a part of a diabetes management system deliver small doses of insulin continuously throughout the day. This continuous delivery of small doses of insulin is often referred to as basal insulin. Each patient may need more or less insulin at certain times of the day based on a variety of factors. Many insulin pumps/diabetes management systems allow the patient to carve up a period of time into different time segments and to enter a rate of basal insulin delivery they desire during each individual time segment. Generally, users can create multiple time segments over a 24 hour period. The variable rates of insulin delivery within the time segments over 24 hours can define a basal program.

Conventional insulin pumps/diabetes management systems and their corresponding user interfaces require the user to manually enter start and end times to define a time segment and to manually enter the basal rate for each time segment in a tabular format. Basal programs are then displayed to the user in a time-based tabular format for confirmation. In contrast to these conventional systems and user interfaces, the user interface and techniques described herein allow the user to optionally view a static basal program graph after the basal program is completed and saved. Further, the user interface and techniques described herein enables a graph or timeline of the basal program to be displayed in real-time as the user builds the basal program. Specifically, the user interface and techniques described herein provides a graph showing the basal rates for each time segment as the basal program is built, thereby improving the experience of the user. The basal program can then be used to direct the delivery of insulin to the user—e.g., by having the basal program built on the portable electronic device 100 transferred to the drug delivery device 114 as instructions for implementation.

In various embodiments, the user interface and techniques described herein present a real-time basal program graph as the user builds her basal program. For example, at each step of the process, the graph can change to reflect the user's input and can immediately show the user the effect of the data that is entered as the user builds a basal program. FIGS. 2-8 illustrate various embodiments of a user interface for building and depicting a basal program. The various embodiments depicted in FIGS. 2-8 can be provided by the portable electronic device 100 as part of a diabetes management system/insulin delivery system as described herein (e.g., within the drug delivery system 112).

Figure 2:
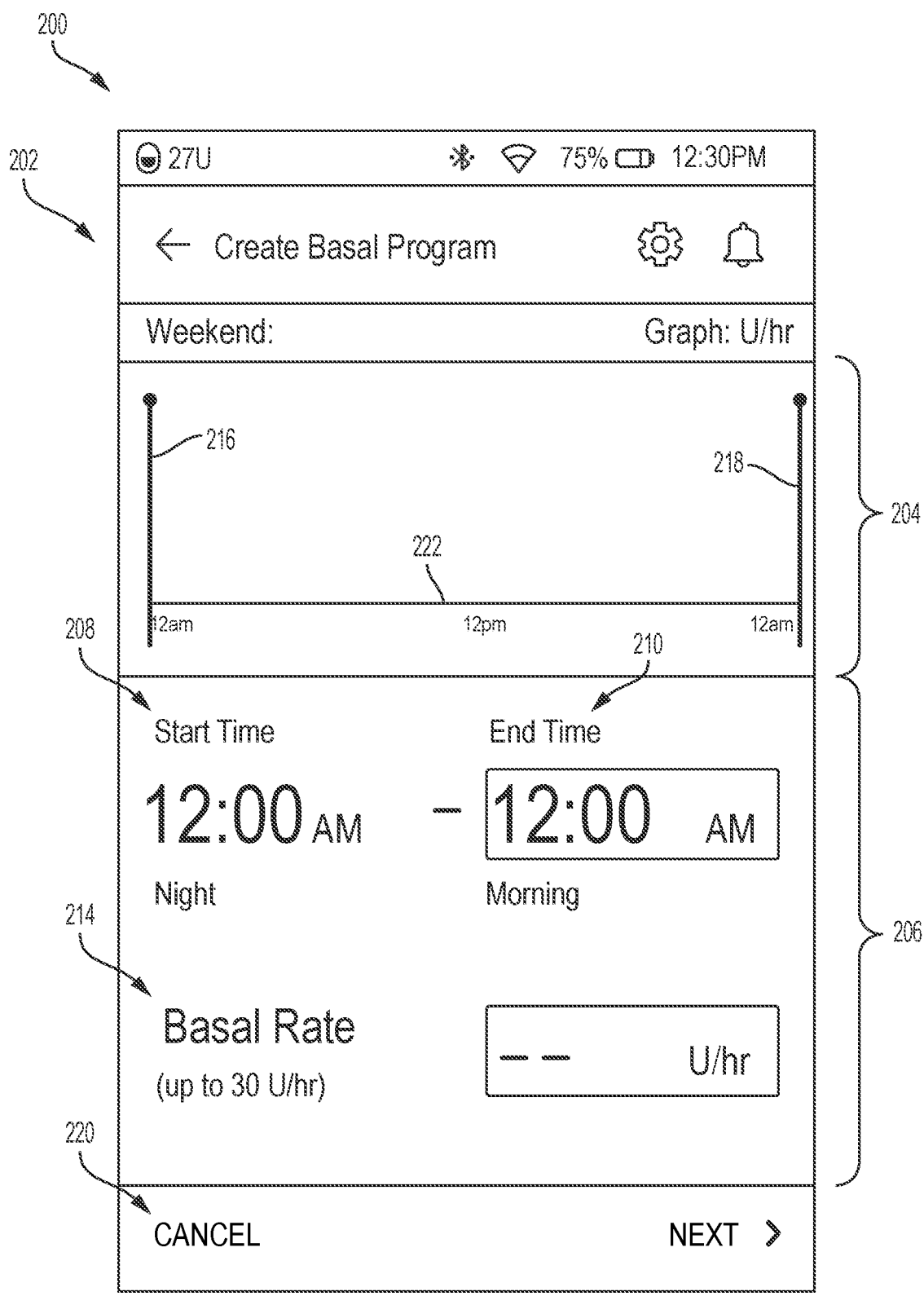
FIG. 2 illustrates a first exemplary user interface for creating a basal program.

FIG. 2 illustrates an exemplary user interface 200 for initially starting or creating a basal program. That is, FIG. 2 illustrates the user interface 200 provided to a user when the user first selects the option of adding or building a new basal program. The user interface 200 can be presented on the touchscreen of the portable electronic device 100 as described herein.

As shown in FIG. 2, an identifier 202 specifies the type of program or mode being presented by the user interface 200. As shown, the identifier 202 specifies that the user interface 200 is presenting an interface for building a basal program (e.g., by indicating "Create Basal Program" as shown).

A first portion of the user interface 204 can provide a graphical area of the user interface 200. In particular, the graphical area 204 can be used to display data graphically or to enter or receive input data from a user in a graphical manner.

A second portion of the user interface 206 can provide a textual area of the user interface 200. In particular, the textual area 206 can be used to display data textually or to enter or receive input data from the user in a textual manner.

Within the textual area 206, various data labels or descriptions and corresponding data values can be presented. Specifically, a start time 208, an end time 210, and a basal rate 214, along with corresponding values, can be presented. In various embodiments, as a default or as part of an initial presentation to the user, the start time 208 and end time 210 can be set to or can define a 24 hour interval. Additionally, a default basal rate 214 can be presented or a not yet defined basal rate 214 can be presented. The user, by interacting with the touchscreen on which the user interface 200 is presented, can adjust the start time 208, the end time 210, and the basal rate 214 by touching the corresponding value indicator areas and entering new values (e.g., through a pop-up keyboard or scroll wheel or other user input selection tool).

The start time 208 and end time 210 depicted textually in the area 206 can be depicted graphically in the area 204 on a timeline 222. In particular, a start bar 216 can graphically represent the start of a basal program time interval. As shown in FIG. 2, the start bar 216 graphically depicts the start time 208 on the timeline 222 (e.g., the start bar 216 is depicted along the timeline 222 at a position corresponding to the start time 208). Similarly, an end bar 218 can graphically represent the end of a basal program time interval. As shown in FIG. 2, the end bar 218 graphically depicts the end time 210 on the timeline (e.g., the end bar 218 is depicted along the timeline 222 at a position corresponding to the end time 210). The timeline 222 can initially graphically depict a 24 hour interval of time.

Area 220 of the user interface 200 can enable a user to select actions related to building a basal program. Specifically, the area 220 provides a user with a mechanism for indicating a particular basal program should be canceled or should proceed to a next step.

The user interface 200 depicted in FIG. 2 (as well as all user interfaces depicted herein) can be provided on a touchscreen such that a user can touch and enter or manipulate any presented data. For example, the graphical area 204 can graphically depict any data shown or manipulated by the user in the textual area 206, such that altering the data shown in the textual area 206 is reflected graphically in the area 204. For example, when the user adjusts the value of the start time 208, the depicted position of the start bar 216 along the timeline 222 can be adjusted dynamically as the adjustment is made. Similarly, when the user adjusts the value of the end time 210, the depicted position of the end bar 218 along the timeline 222 can be adjusted dynamically as the adjustment is made. Accordingly, the start bar 216 and end bar 218 can slide along the timeline 222 as the user adjusts the values of the start time 208 and end time 210, respectively, within the area 206.

Correspondingly, the textual area 206 can textually depict any data shown or manipulated by the user in the graphical area 204, such that altering the data shown in the graphical area 204 is reflected textually in the area 206. For example, a user may engage and manipulate the start bar 216 and can slide it along the timeline 222. In response, the start time 208 can be dynamically updated to reflect the time value corresponding to the depicted position of the start bar 216 along the timeline 222. In various embodiments, a user can only enter or manipulate data values in the textual area 206 and the graphical area 204 is only used to graphically represent data shown and adjusted by a user in the textual area 206.

In various embodiments, the graphical area 204 can present the timeline 222 in a manner such that it can be broken into different time segments. The user can then specify corresponding basal rates for each time segment defined by the user as shown in the exemplary user interfaces depicted in FIGS. 3-8 and described in more detail below.

Figure 3:
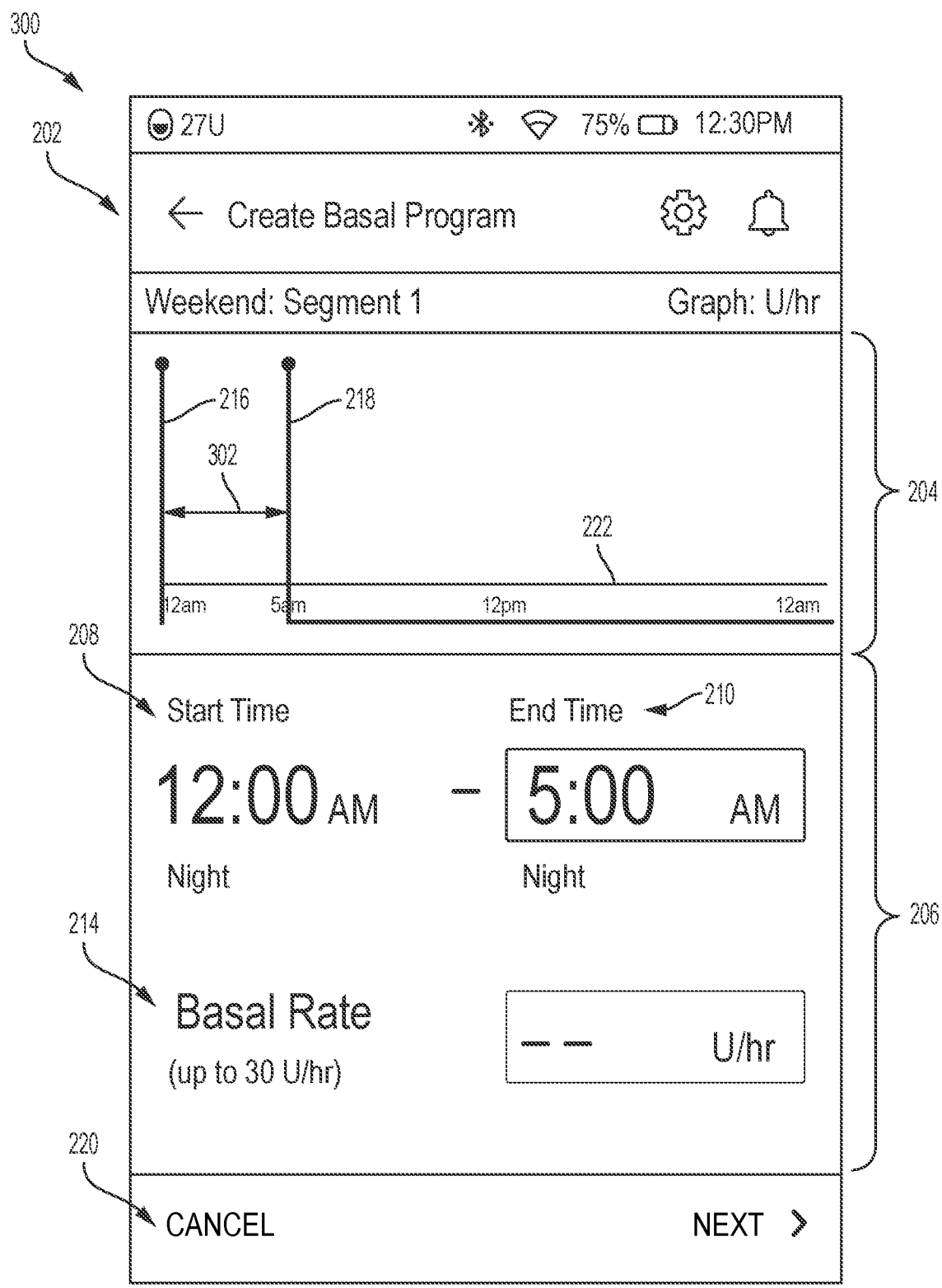
FIG. 3 illustrates a second exemplary user interface for creating a basal program.

FIG. 3 illustrates an exemplary user interface 300 for defining a first time segment 302. To enter the end of the first time segment 302, a user can first tap on the end time 210 label or icon or corresponding data value and can then subsequently enter an end time value. The end time value can be selected using, for example, a scroll wheel that appears when the user taps on the user interface 300 (not shown in FIG. 3).

Once the user selects an end time value, the end bar 218 can move to the corresponding position on the timeline 222—to match the value shown by the end time indicator 210. As a result, the area between the start bar 216 and the end bar 218 can visually depict the first time segment 302. As the user scrolls through possible values of the end time, the end bar 218 can dynamically move to illustrate the changing duration of the first time segment 302 as the user manipulates the duration through data entry. In various embodiments, the user can drag the end bar 218 along the timeline 222 to a position corresponding to a desired end time value to define the first time segment 302.

Figure 4:
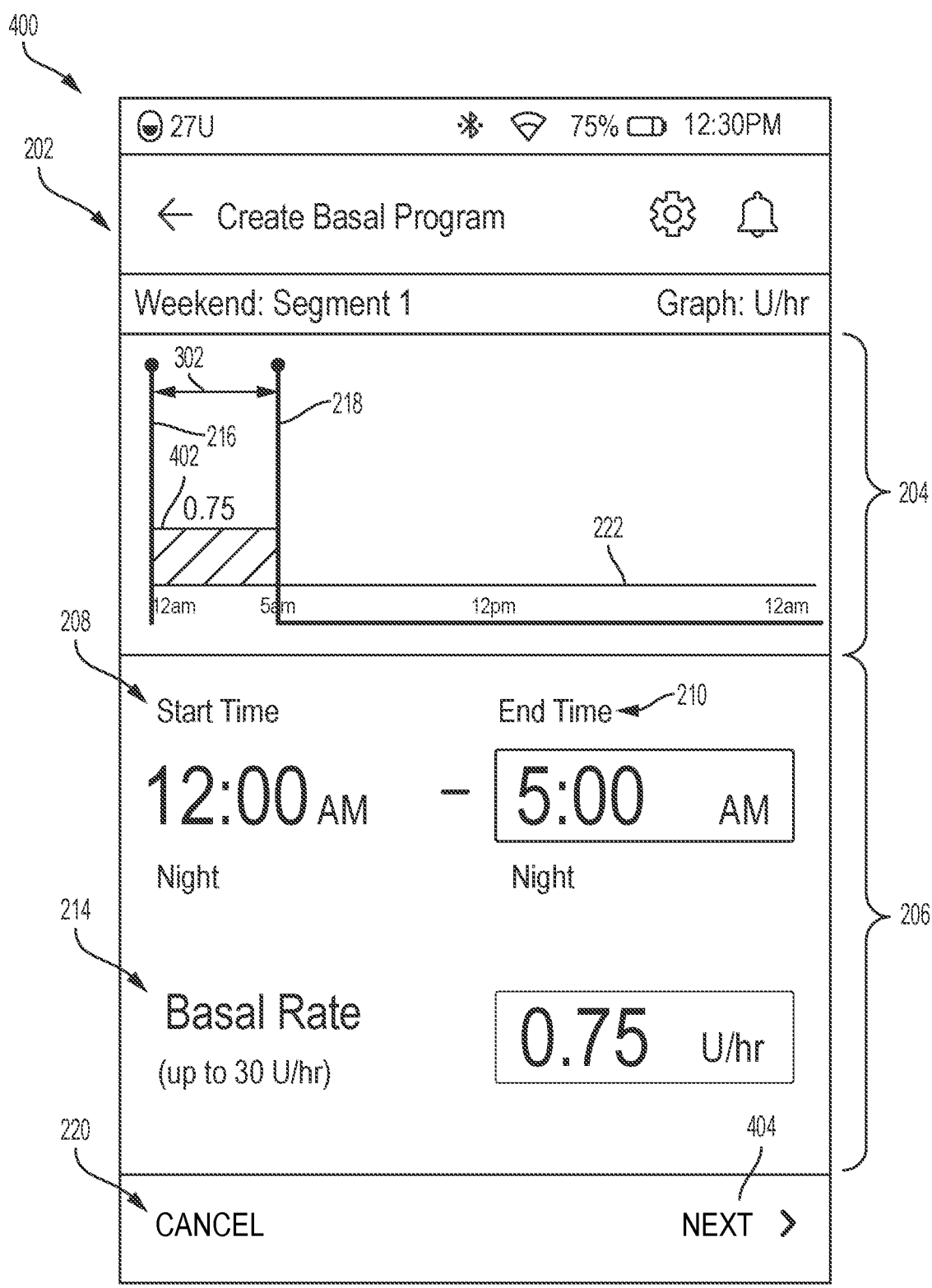
FIG. 4 illustrates a third exemplary user interface for creating a basal program.

FIG. 4 illustrates an exemplary user interface 400 for defining a first basal rate for the first time segment 302. To enter the basal rate for the first time segment 302, the user can tap on the basal rate 214 label or icon or corresponding data value and then subsequently enter a basal rate value. The basal rate can be selected using, for example, a scroll wheel that appears when the user taps on the user interface 400 (not shown in FIG. 4).

In various embodiments, as the user scrolls the wheel to select the basal rate, indicator 402 dynamically shows the changing basal rate. The indicator 402 can be positioned between the start bar 216 and the end bar 218. A height or thickness of the indicator 402 (e.g., relative to the timeline 222) can correspond to the basal rate being selected. For example, the indicator 402 can increase or decrease dynamically as a user scrolls through various basal rate possibilities, thereby automatically reflecting possible basal rates graphically for the selected time segment (e.g., the first time segment 302) defined as the period of time between the start bar 216 and the end bar 218. The indicator 402 can be a horizontally oriented bar with a thickness proportional to a selected basal rate such that higher basal rates are represented by a relatively thicker bar and lower basal rates are represented by a relatively thinner bar. Once a user settles on a basal rate as depicted by the indicator 402, the user can tap on the next icon 404 to move on to creating a second time segment.

Figure 5:
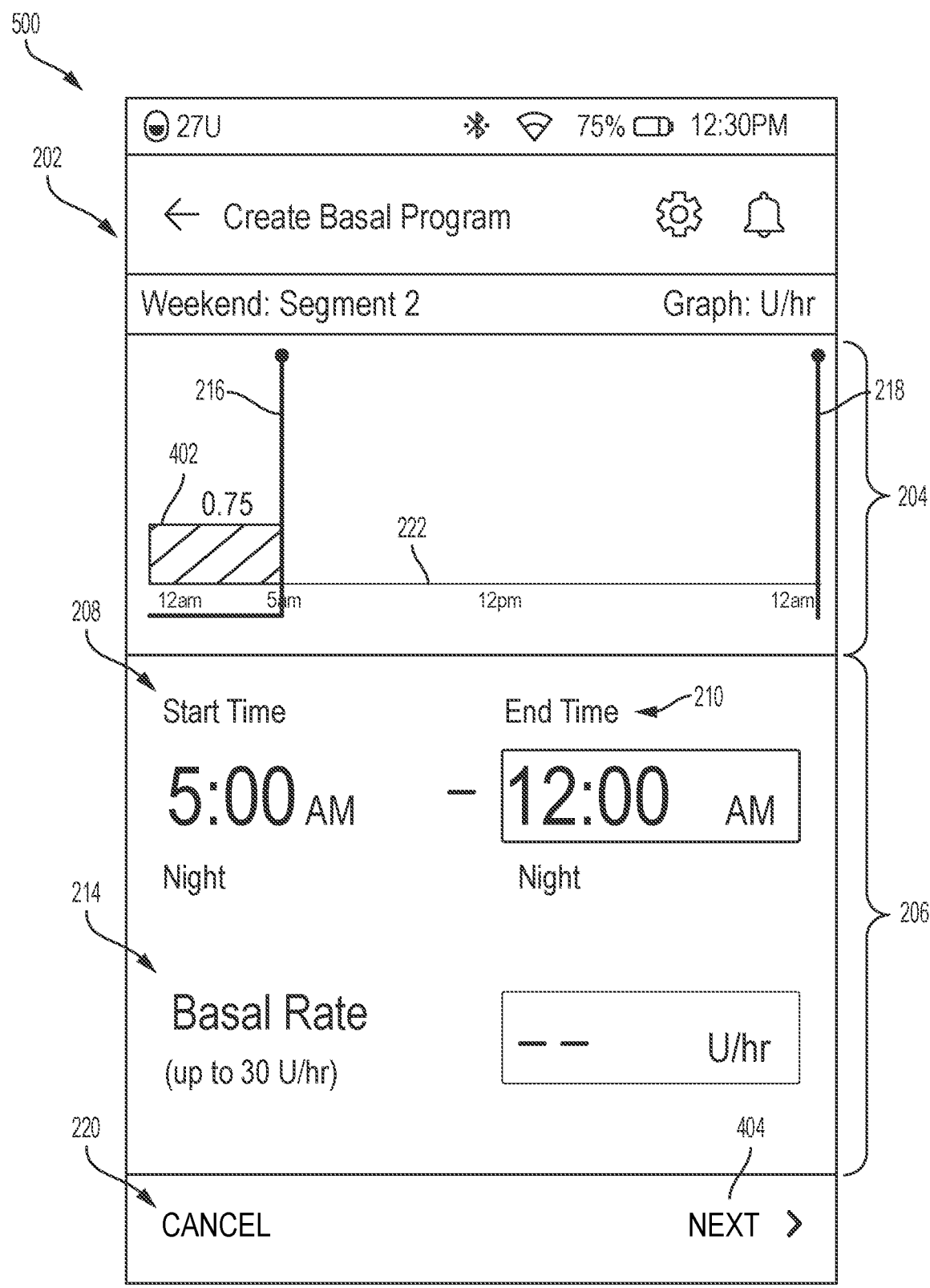
FIG. 5 illustrates a fourth exemplary user interface for creating a basal program.

FIG. 5 illustrates an exemplary user interface 500 for initiating creation of a subsequent time segment. Once a time segment has been defined and a corresponding basal rate selected (e.g., for the first time segment 302), a user can provide an input indicating that she is ready to define a subsequent time segment (e.g., by tapping the next icon 404 as shown in FIG. 4).

To begin the process of defining another time segment, the user interface 500 can automatically move the start bar 216 to the end time of the prior time segment (e.g., the end of the first time segment 302). The start time 208 can reflect the change or movement of the start bar 216. Further, the end bar 218 can default to the end of the entire time segment (e.g., the end of the 24 hour period shown by the timeline 222). The end time 210 can reflect the change or movement of the end bar 218.

A default basal rate can also be selected and depicted by the user interface 500. Specially, the basal rate for the subsequent time segment being defined can default to the value of the immediately prior segment (e.g., as shown by indicator 402 for the first time segment 302). Alternatively, as shown in FIG. 2, the basal rate for the subsequent time segment can initially be undefined and unspecified.

Figure 6:
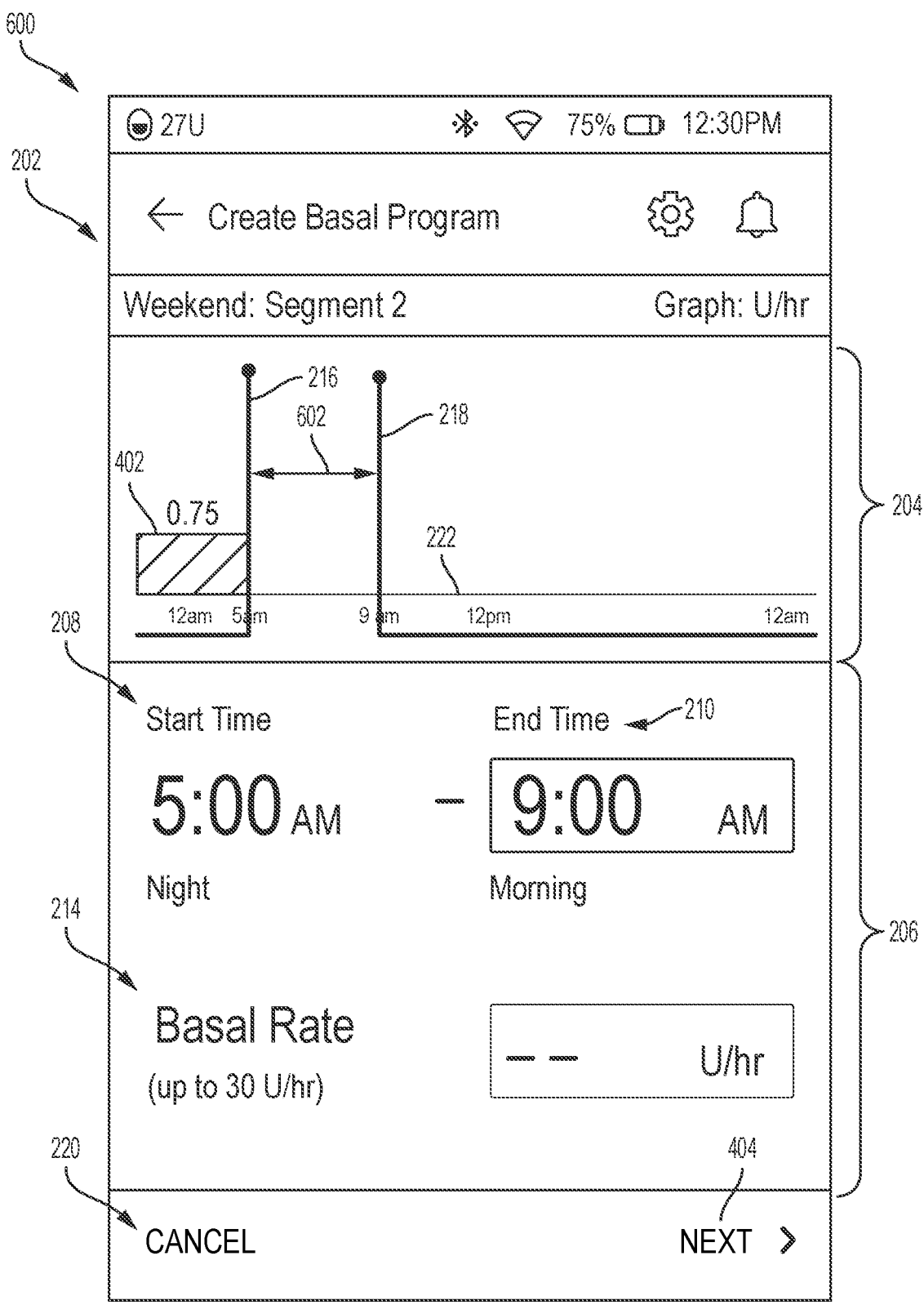
FIG. 6 illustrates a fifth exemplary user interface for creating a basal program.

FIG. 6 illustrates a user interface 600 for completing creation of the subsequent time segment which can form a second time segment 602. Similar to defining the end of the first time segment 302, to enter the end time for a second time segment 602, a user can tap on the end time 210 label or icon or corresponding data value and then subsequently enter an end time value. The end time value can be selected using, for example, a scroll wheel that appears when the user taps on the user interface 600 (not shown in FIG. 6).

Once the user selects an end time value, the end bar 218 can move to the corresponding position on the timeline 222—to match the user entered end time 210. As a result, the area between the start bar 216 and the end bar 218 can visually depict the second time segment 602.

Figure 7:
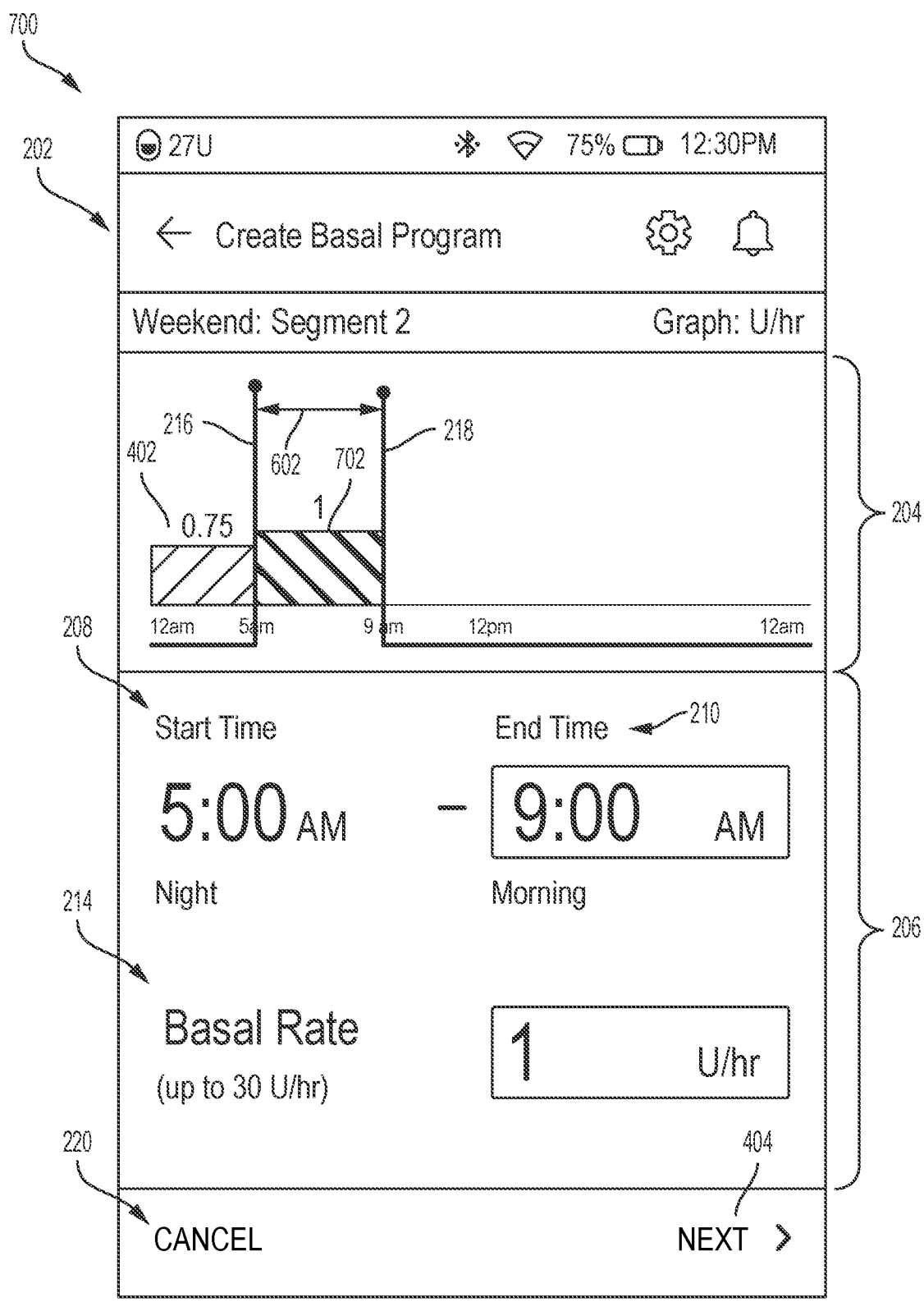
FIG. 7 illustrates a sixth exemplary user interface for creating a basal program.

FIG. 7 illustrates an exemplary user interface 700 for defining a basal rate for the second time segment 602. To enter the basal rate for the second time segment 602, the user can tap on the basal rate 214 label or icon or corresponding data value and then subsequently enter a basal rate value. The basal rate can be selected using, for example, a scroll wheel that appears when the user taps on the user interface 700 (not shown in FIG. 7).

In various embodiments, as the user scrolls the wheel to select the basal rate, indicator 702 dynamically shows the changing basal rate. The indicator 702 can be positioned between the start bar 216 and the end bar 218. A height or thickness of the indicator 702 can correspond to the basal rate being selected. For example, the indicator 702 can increase or decrease dynamically as a user scrolls through various basal rate possibilities, thereby automatically reflecting possible basal rates graphically for the selected time segment (e.g., the second time segment 602) defined as the period of time between the start bar 216 and the end bar 218. The indicator 702 can be a horizontally oriented bar with a thickness proportional to a selected basal rate such that higher basal rates are represented by a relatively thicker bar and lower basal rates are represented by a relatively thinner bar.

Once a user settles on a basal rate as depicted by the indicator 702, the user can tap on the next icon 404 to move on to creating another time segment. Until a user indicates that she has settled on a particular time segment and corresponding basal rate, the indicator 702 can remain a different color or shade of color relative to the indicator 402 to indicate that the particular time segment and basal rate are not fully set. In various embodiments, the user interface 700 can indicate the not yet completed basal rate and time segment selection through different colors, shading, icons or other graphical depictions on the timeline.

The process for defining time segments and corresponding basal rates can be repeated until the user has defined time segments and corresponding basal rates for an entire 24 hour period (or for any desired period of time). The user interface described herein enables any number of time segments to be defined and any basal rate to be selected.

Figure 8A:
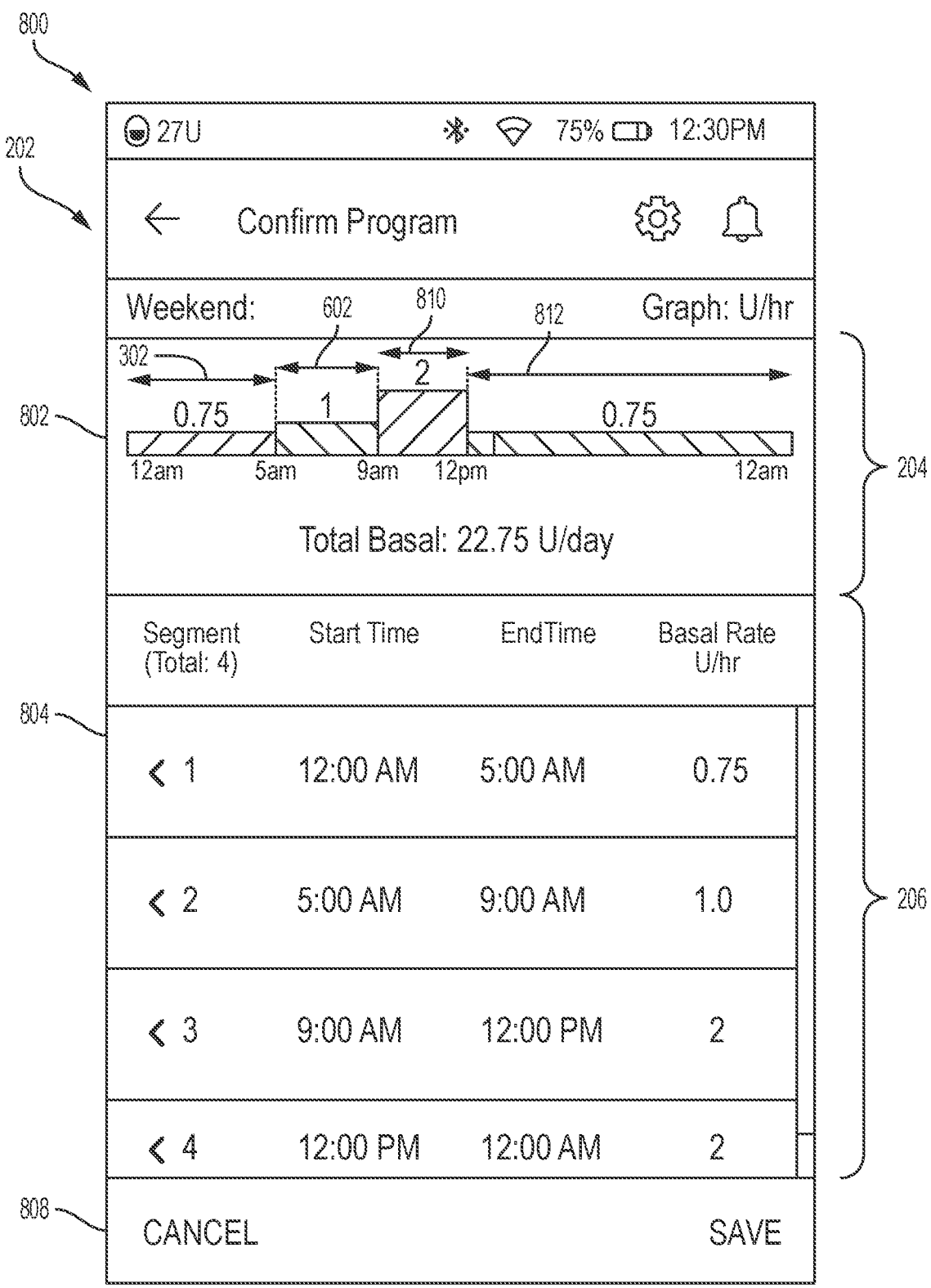
FIG. 8A illustrates a first exemplary user interface relating to the basal program created using the user interfaces depicted in FIGS. 2-7.

FIG. 8A illustrates an exemplary user interface 800 for reviewing and saving a basal program. As shown in FIG. 8A, an entire 24 hour period of time has been broken into different time segments having corresponding basal rates—including first and second time segments 302 and 602 and additional time segments 810 and 812. The graphical area 204 of the user interface 800 provides a visual preview 802 of the entire basal program that the user has entered—for example, the defined time segments and corresponding basal rates. The visual preview 802 graphically depicts each time segment and corresponding basal rate values relative to all other time segments and basal rates. Further, the textual area 206 provides a tabular listing 804 of the time segments and basal rate values as depicted in the visual preview 802. In this way, the user interface 800 provides both a visual representation 802 and a tabular representation 804 of the basal program for the user.

As further shown in FIG. 8A, the user interface 800 can include a menu area 808. The menu area allows a user to either cancel or save the current (e.g., depicted) basal program.

Figure 8B:
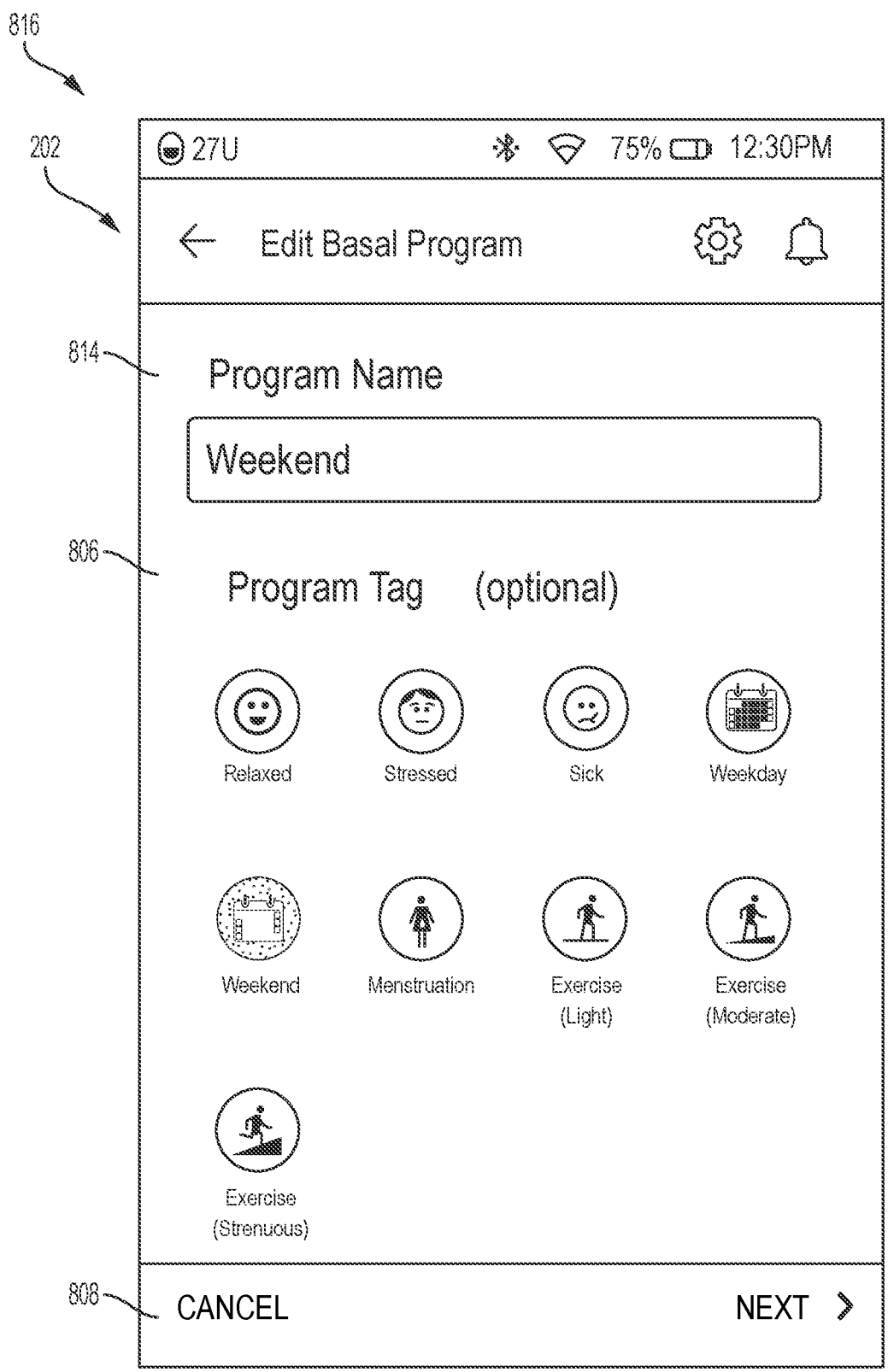
FIG. 8B illustrates a second exemplary user interface relating to the basal program created using the user interfaces depicted in FIGS. 2-7.

FIG. 8B illustrates an exemplary user interface 816 for further reviewing and saving a basal program. As shown in FIG. 8B, the user interface 816 can provide an area 814 for a user to enter a name for the basal program. Further, the user interface 816 can allow a user can to tag or label the type of basal program created using the tags or labels 806. The user interface 816 can be presented when creation of a basal program is first initiated or after the basal program has been defined and a user would like to save and tag the program.

The user interfaces described in relation to FIGS. 2-8 provide numerous benefits over conventional user interfaces. The user interfaces described herein allow a user to view a basal program graphically in real-time as the user builds the program. A correct basal profile is key to diabetes management. It is therefore very important that a user's basal program is correctly established. Many individuals understand the basal program information better when it is presented graphically. Market testing has revealed that many users are overwhelmed when only presented with basal program data in a tabular format. Overall, the user interfaces described herein provide the following: (a) enable patients to better understand the variability of their basal rates throughout the day; (b) decrease the cognitive load of understanding a basal program solely through numbers via tabular display only; and (c) make it easier for patients to create and edit basal profiles. As a result, patients using the user interfaces described herein are more likely to adjust basal rates more frequently in conjunction with their health care providers, thereby contributing to better blood glucose control and improved health outcomes.

The basal program built by a user (e.g., as shown graphically in the preview 802) can be used to direct operation of a drug delivery device. In various embodiments, the basal program built on the portable electronic device 100 can be transmitted to the drug delivery device 114 as a set of instructions directing the drug delivery device 114 to deliver the defined amounts of insulin (e.g., by specifying different basal rates) over different periods of time (e.g., by specifying different time segments for each different basal rate). The drug delivery device 114 can use the provided information regarding the basal program to deliver insulin to the user in accordance with the basal program defined by the user.

Temporary Basal Programming Graph

Many diabetes management systems/insulin delivery systems (e.g., insulin pumps) allow a patient to temporarily change a preset basal rate for a certain period of time (e.g., usually less than 12 hours). Conventional diabetes management systems/insulin delivery systems typically require the user to enter a percentage (%) variation from the basal profile or a rate of basal insulin (e.g., in U/hr.) and the duration of the temporary basal rate. Once the temporary basal rate has been confirmed, the conventional diabetes management systems/insulin delivery systems display the new basal rate in U/hr. and often the time remaining on the temporary setting. Accordingly, these conventional systems are generally limited to displaying the modified information in a textual or tabular format. The user interfaces described herein provide an improved user experience by graphically displaying the temporary basal rate over the full duration to the user.

FIGS. 9-13 illustrates various embodiments of a user interface for modifying a basal program. The various embodiments depicted in FIGS. 9-13 can be provided by the portable electronic device 100 as part of a diabetes management system/insulin delivery system (e.g., as part of the drug delivery system 112).

Figure 9:
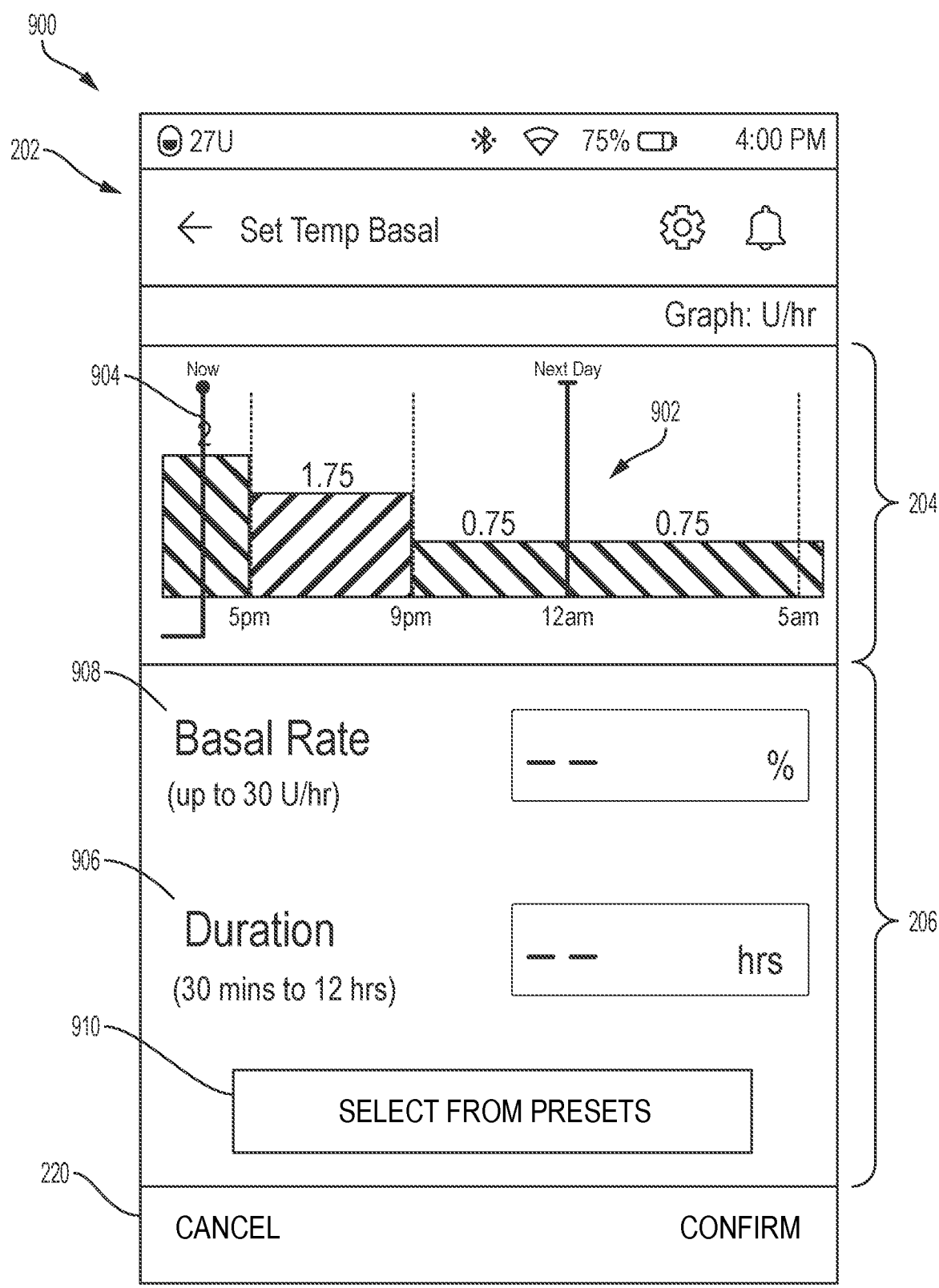
FIG. 9 illustrates a first exemplary user interface for modifying a preset basal program.

FIG. 9 illustrates an exemplary user interface 900 for initially starting a temporary basal program and/or modifying temporarily a preset basal program. That is, FIG. 9 illustrates the user interface 900 provided to a user when the user first selects the option of temporarily modifying basal rates set from a basal program.

As shown in FIG. 9, within the graphical area 204, a graphical representation 902 of a basal program is shown (e.g., similar to the preview 802 shown in FIG. 8A). The identifier 202 indicates that a temporary adjustment to a basal program is being established. A start bar 902 indicates a starting time of the temporary basal rate adjustment. By default, the start bar 904 can start at a current time (e.g., labeled as "Now"). The textual area 206 of the user interface 900 includes a duration identifier 906 and a basal rate identifier 908. The duration and basal rate identifiers 906 and 908 can further include default data (e.g., prior to any adjustment) or can indicate that values are not yet specified or defined (as shown in FIG. 9). The user interface 900 can further include an input 910 for selecting adjustments from already stored presets (e.g., preset adjustments stored in the memory 110).

Figure 10:
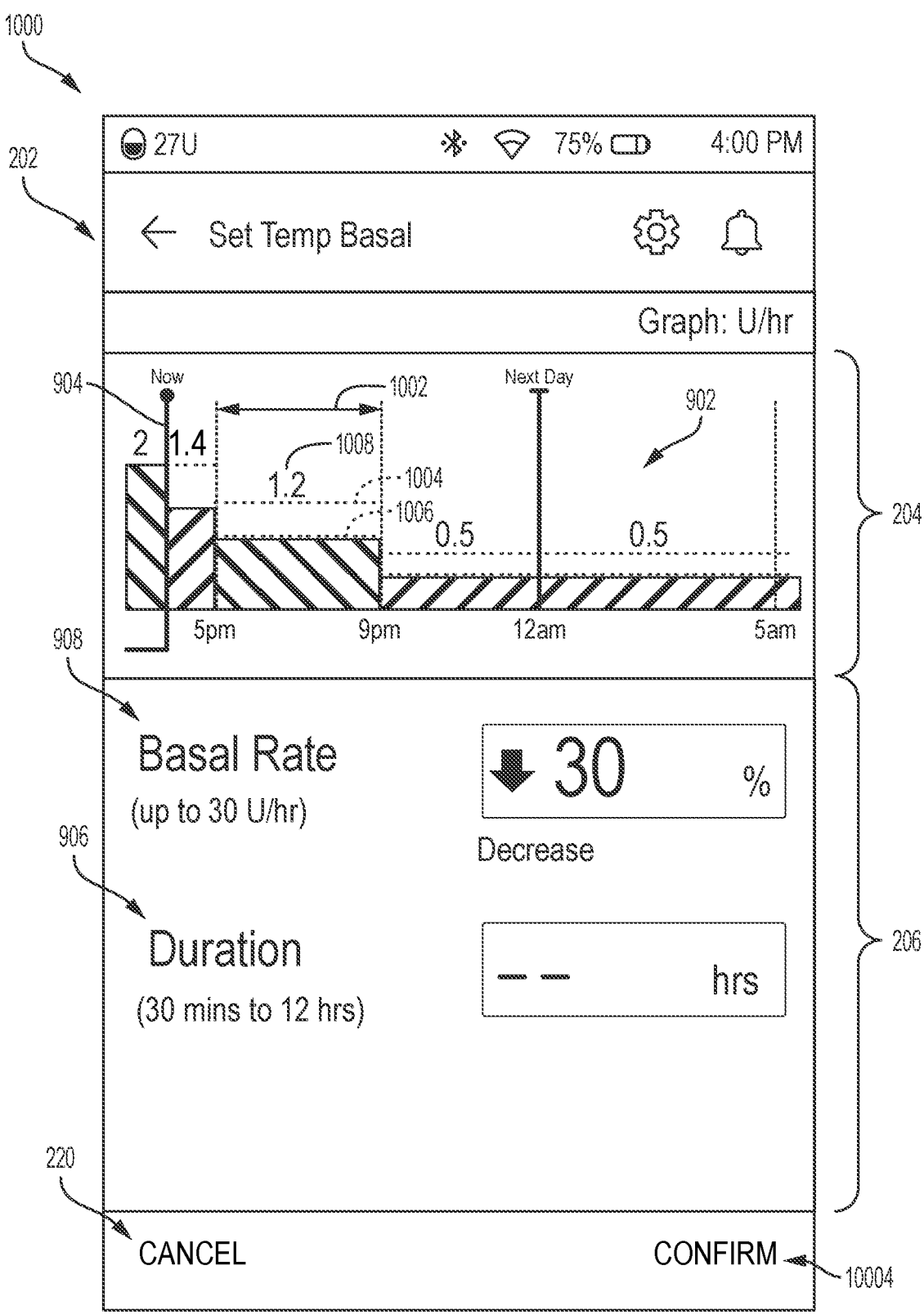
FIG. 10 illustrates a second exemplary user interface for modifying a preset basal program.

FIG. 10 illustrates an exemplary user interface 1000 when a decreased temporary basal rate relative to an initial basal rate is entered or specified by the user. To adjust the basal rate, a user can tap on the basal rate identifier and/or value 908. In various embodiments, tapping on the basal rate identifier or value 908 can cause the user interface 1000 to present a scroll wheel for the user to manipulate (not shown in FIG. 10). The scroll wheel can allow a user to increase or decrease the basal rate for the basal program shown in the graphical area 204. When the user selects a basal rate that is lower than the preset basal rate, the graphical section 204 can show the basal rate adjustment dynamically. Specifically, the basal rate adjustment can be shown by indicating the new basal rate relative to the prior basal rate.

As an example, for a time segment 1002, the initial or prior basal rate is shown by indicator 1004 and the new or adjusted basal rate is shown by indicator 1006. The indicators 1004 and 1006 can be shown by any graphical means such as text, lines, colors or shading. As shown in FIG. 10, the prior basal rate is indicated by a dotted or dashed line 1004 such that the distance between the line 1004 and the indicator 1006 represents the change in basal rate (e.g., corresponding to the value specified by the basal rate input 908). The area between the indicator 1004 and 1006 can be colored or shaded or depicted in any manner to indicate the change. The time segment 1002 can also depict the new value 1008 of the adjusted basal rate. The representations of the basal rate changes shown with respect to the time segment 1002 can be similarly shown in the other time segments of the displayed basal program. If a user is satisfied with the changes to the basal rate, an input 1004 can be selected by the user to confirm or lock in the changes to the basal rate.

Figure 11:
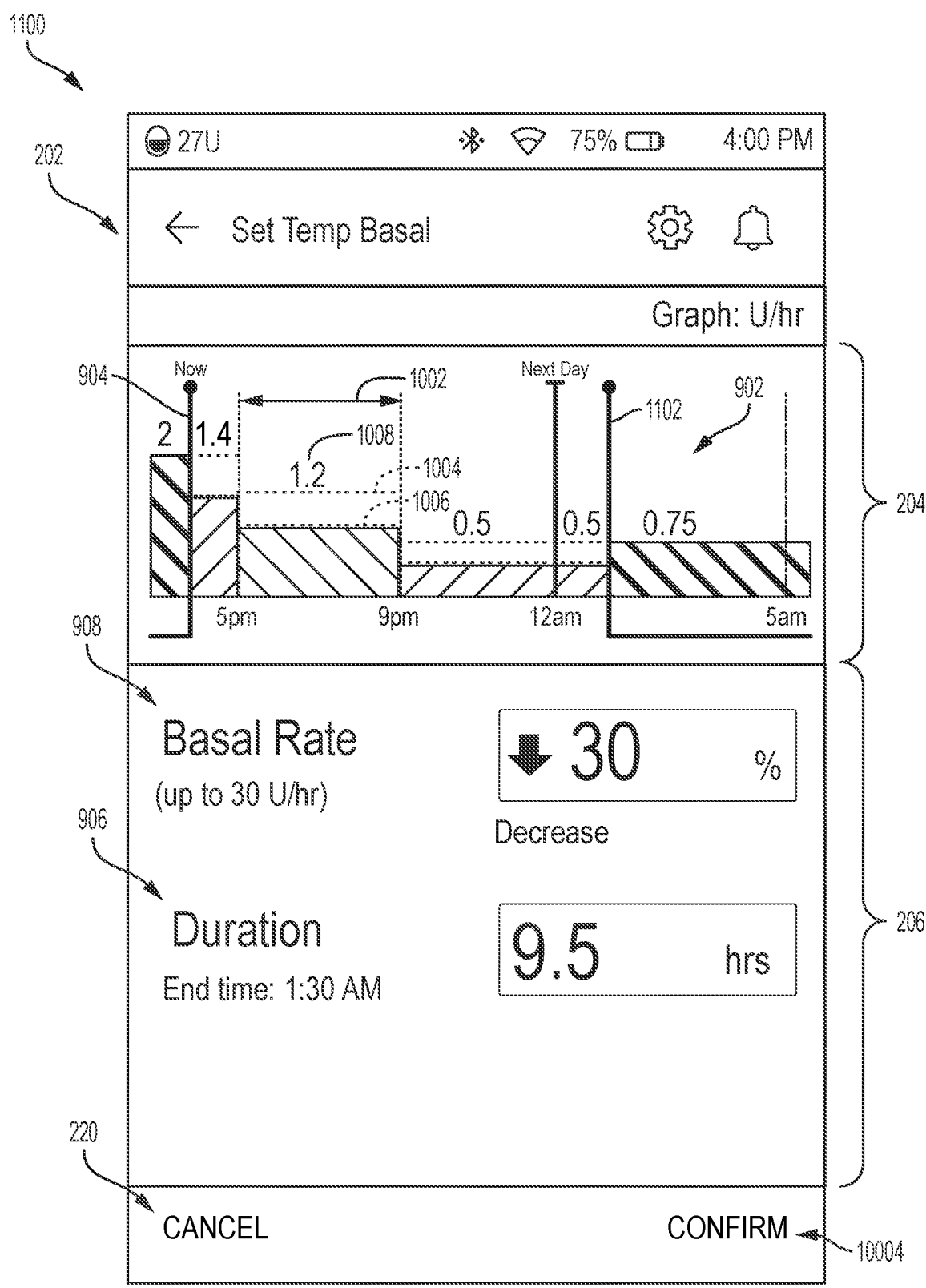
FIG. 11 illustrates a third exemplary user interface for modifying a preset basal program.

FIG. 11 illustrates an exemplary user interface 1100 for entering a duration of the temporary basal adjustment period. To set a duration, a user can tap on the duration value 906 and can select a duration value. In various embodiments, tapping on the duration value 906 can cause the user interface 1100 to present a scroll wheel for the user to manipulate (not shown in FIG. 11). As the user adjusts the duration value 906, an end bar 1102 dynamically moves along the timeline 222 shown in the graphical area 204. As a result, the start bar 904 and the end bar 1102 dynamically display the duration of the temporary basal program. Once a duration value is selected, the end bar 1102 can stop moving. The duration value 906 will reflect the duration value graphically depicted in the area 204.

Accordingly, FIG. 10 illustrates the user interface 1000 for specifying the change (e.g., as a percent change) in the basal rate and FIG. 11 illustrates the user interface 1100 for specifying the duration (e.g., as an amount of time) of the temporary basal rate and program adjustment. Once a user specifies the change and duration, the user can confirm the changes. The adjustments to any time segment can then be used to adjust delivery of insulin to the user as described above in relation to the drug delivery system 112.

Figure 12:
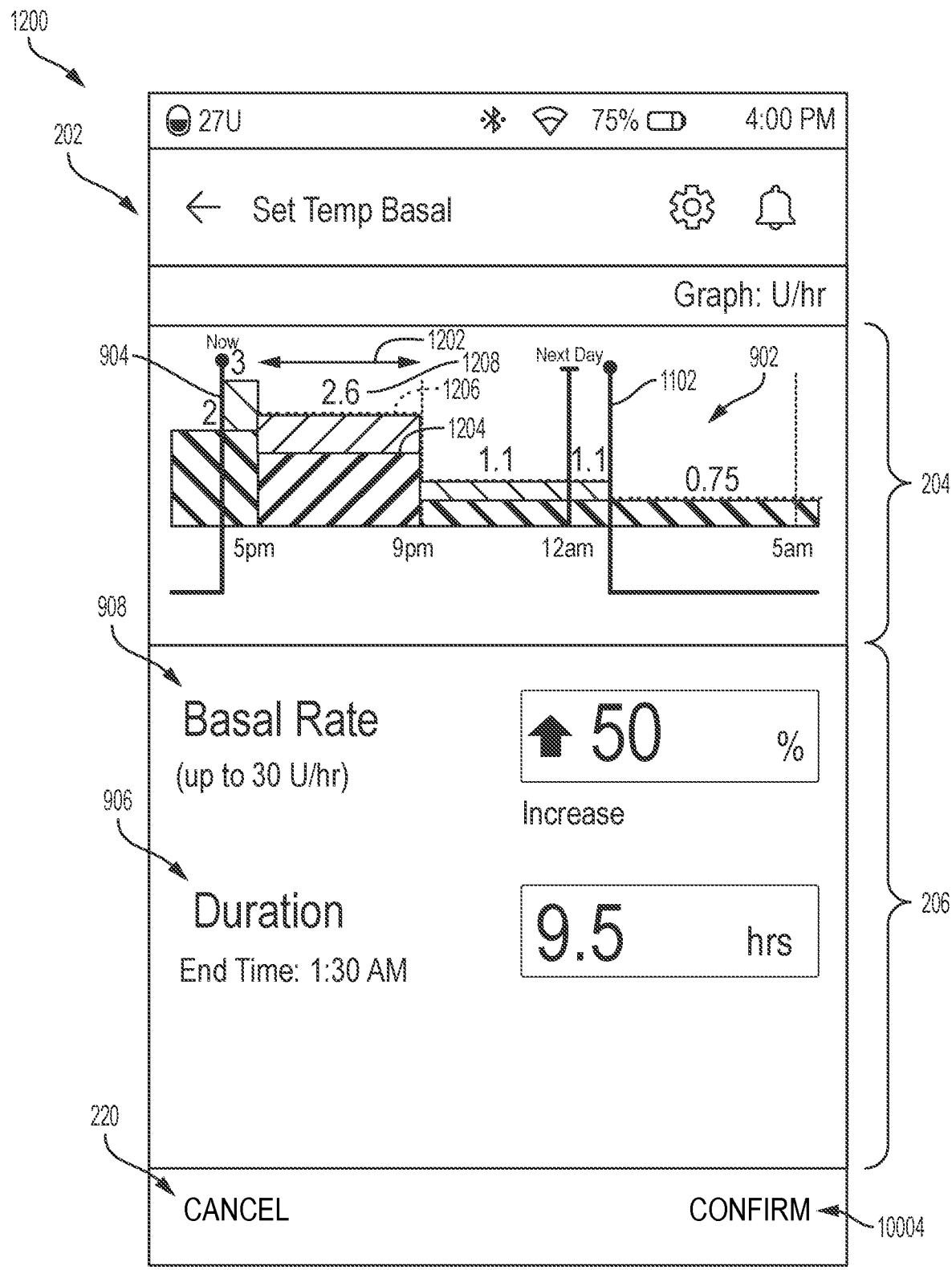
FIG. 12 illustrates a fourth exemplary user interface for modifying a preset basal program.

FIG. 12 illustrates an exemplary user interface 1200 showing adjustment of a basal program with an increased temporary basal rate. The basal rate can be adjusted to be increased in a manner similar to that discussed above in relation to FIGS. 10 and 11. As an example, for a time segment 1202, the initial or prior basal rate is shown by indicator 1204 and the new or adjusted basal rate is shown by indicator 1206. The indicators 1204 and 1206 can be shown by any graphical means such as text, lines, colors or shading. As shown in FIG. 12, the new or adjust basal rate 1206 is shown as above or on top of the prior or initial basal rate 1206. The difference between the prior rate and the new rate can be indicated by the area between the indicator 1204 and 1206 and can be colored or shaded or depicted in any manner to indicate the change. The time segment 1202 can also depict the new value 1208 of the adjusted basal rate. The representations of the basal rate changes shown with respect to the time segment 1202 can be similarly shown in the other time segments of the displayed basal program. If a user is satisfied with the changes to the basal rate, an input 1004 can be selected by the user to confirm or lock in the changes to the basal rate.

Figure 13:
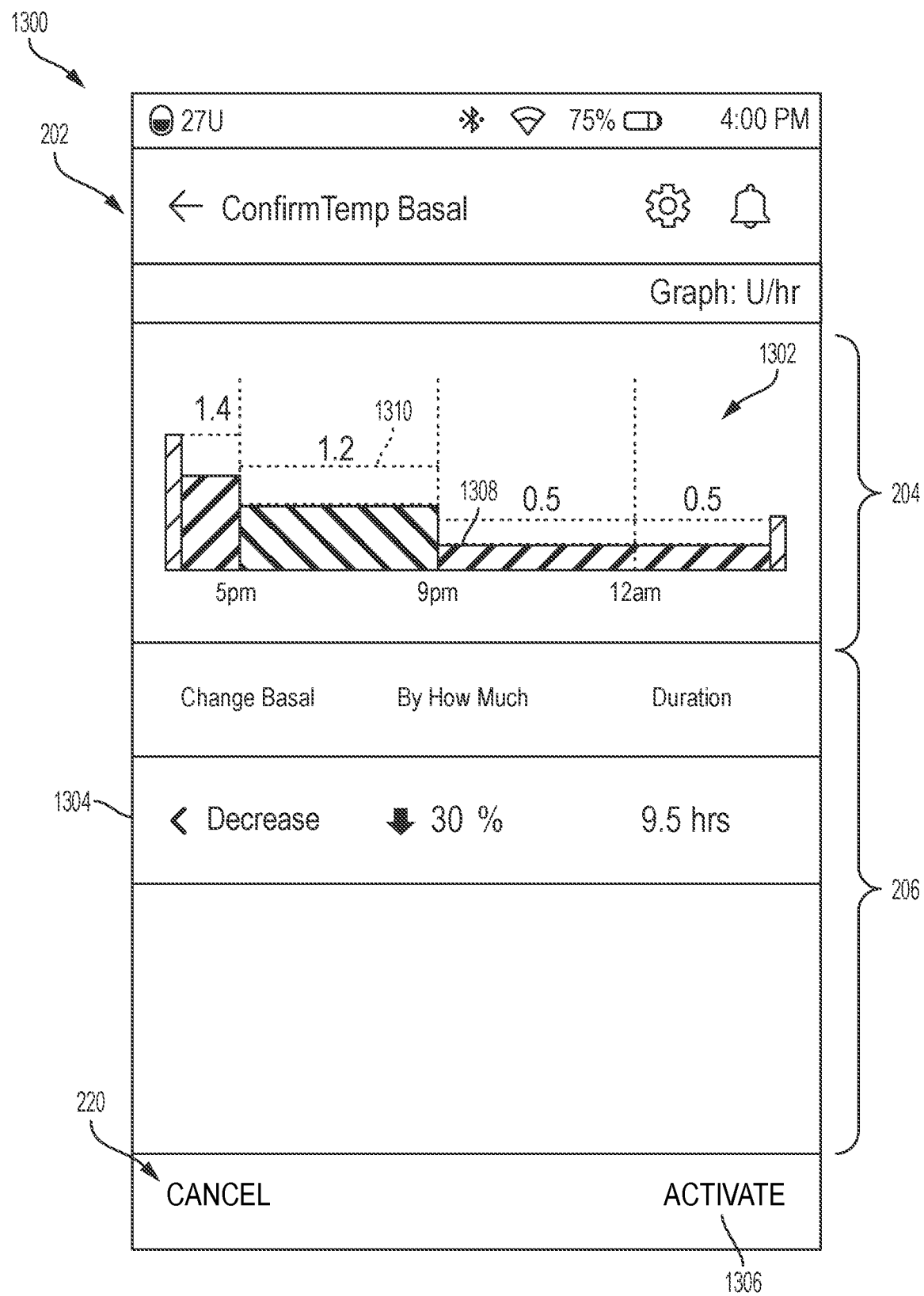
FIG. 13 illustrates a fifth exemplary user interface for modifying a preset basal program.

FIG. 13 illustrates an exemplary user interface 1300 for confirming changes to a basal program and/or confirming temporary changes to a basal rate over a specified period of time. As shown in FIG. 13, once the user completes entry of the temporary basal rate adjustment, the graphical section 204 provides a visual preview graph 1302 of the entire temporary basal period. The graphical section 204 also shows a comparison of the initial basal rate 1310 and the newly selected temporary basal rate 1308 so that a user can compare the changes visually. Further, the textual section 206 provides a tabular listing 1304 indicating the duration of the temporary adjustment and the amount of change (e.g., as a percentage of the initial rate). If the adjustments meet with the user's approval, then the user can use input 1306 to activate the basal rate adjustments.

As with the user interfaces shown in FIGS. 2-8 for providing a user with a real-time basal programming graph, the user interfaces shown in FIGS. 9-13 provide a user with graphical views of a temporary basal programming graph that can aid a user's understanding of the basal rate adjustments. In turn, the user's experience is improved such that more frequent and better adjustments to basal rates are made by the user for improved diabetes management. Further, after activation, the temporary basal adjustments can be transmitted to a drug delivery device for implementation.

Dynamic Keyboard

Figure 14:
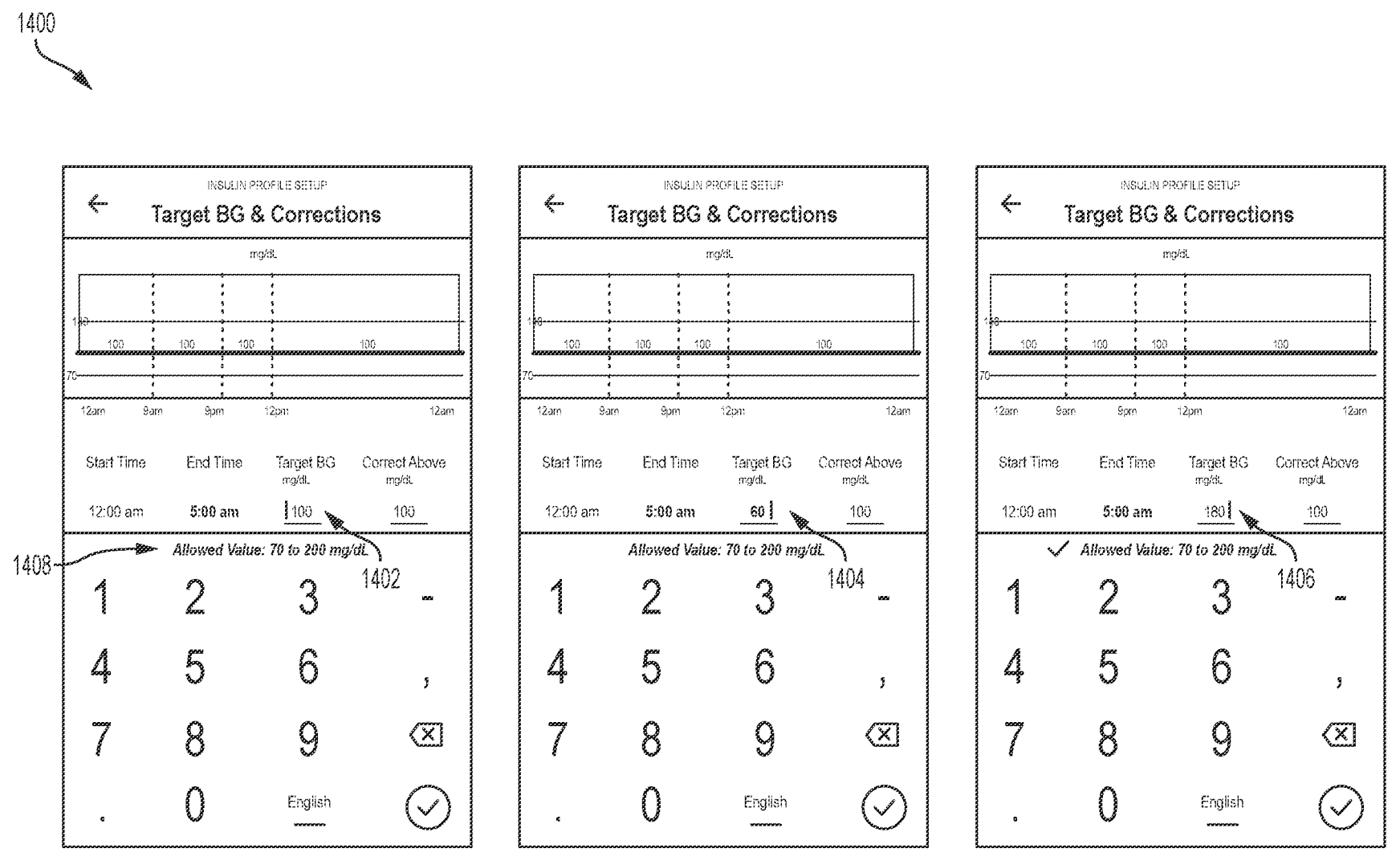

The user interface provided by the portable electronic device 100 can also provide a dynamic keyboard as shown in FIG. 14. The dynamic keyboard can display default values with a first type of text 1402 (e.g., a faded text). User entered values that fall outside of a permissible range can be indicated with a second type of text 1404 (e.g., a red text). User entered values that fall within a permissible range can be indicated with a third type of text 1406 (e.g., a black text or a green text). Dynamic messages 1408 can also be provided to the user when the user enters data values. The dynamic messages 1408 can indicate if certain values are default values, permitted values, or values that fall outside of a permissible range of values. Such indications can be provided via text and by different text colors—for example, a dynamic message 1408 can be provided in red with a message indicating a value is outside a permitted range and can be provided in green with a message indicating a value is within a permitted range. The dynamic keyboard 1400 provides an enhanced user experience and enables a user to quickly determine if an entered value is acceptable or not and can also provide an explanation as to why a value is permitted or not.

Figure 15:
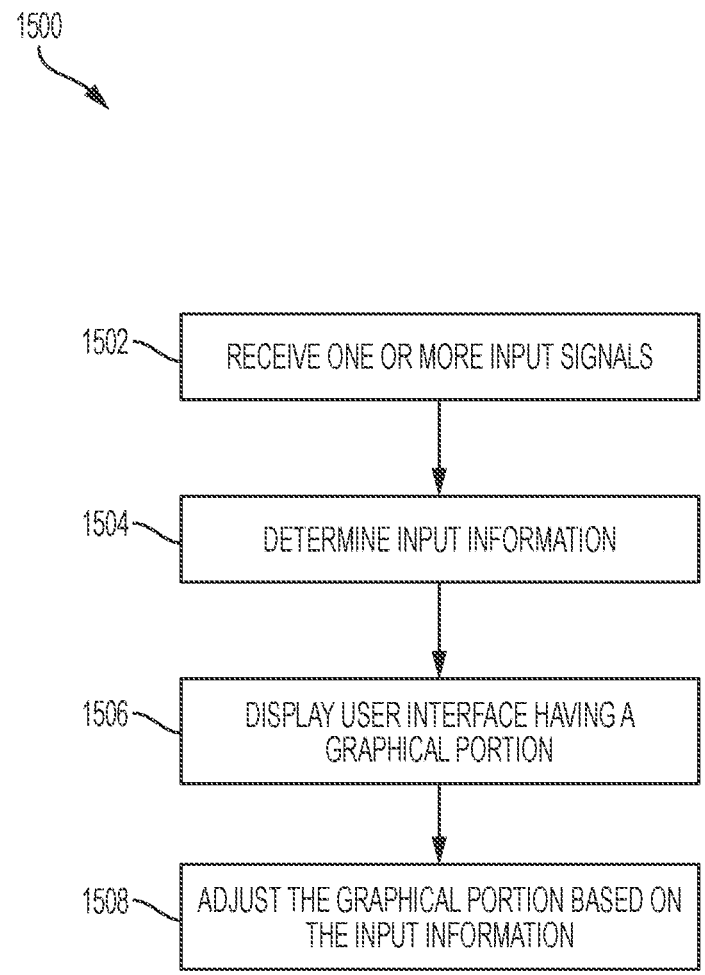
FIG. 15 illustrates an embodiment of a logic flow for providing one or more of the user interfaces depicted in FIGS. 3-14.

FIG. 15 illustrates an embodiment of a logic flow 1500 for providing the user interfaces described herein. The logic flow 1500 may be representative of some or all of the operations executed by one or more embodiments described herein. As an example, the logic flow 1500 can be implemented by the portable electronic device 100 to provide the user interfaces depicted in FIGS. 2-14.

At 1500, one or more input signals can be received. The input signals can originate locally (e.g., by a local user input provided through a touchscreen) or can originate remotely (e.g., by a remote device in communication with a local device implementing the logic flow 1500). At 1500, an input signal receiver, operable on a processor, may be configured to receive one or more input signals from one or more input devices, such as a touchscreen. At 1500, a communications receiver, operable on a processor, may be configured to receive one or more input signals from one or more remote devices.

At 1502, input information from the input signals can be determined. A control module, operable on the processor, may be configured to determine the input information from the one or more input signals. The input information may include instructions and/or data values.

At 1506, a user interface is displayed. The user interface may be displayed on a display device. The display device may be a touchscreen. The user interface can include a graphical portion for displaying information and/or for receiving input information. The control module may cause the display device to display the user interface. The control module may specify graphics or other visual elements stored in a memory for display on the display device.

At 1508, the user interface can be adjusted based on the received input information. The control module can direct the display device to adjust the provided display to provide a dynamically updated user interface responsive to received input information. As an example, the graphical portion can dynamically display a time segment of a basal program as described above in relation to FIGS. 2-8. The graphical portion can dynamically display a basal rate for a time segment of a basal program as described above in relation to FIGS. 2-8. The graphical portion can also display a complete graph of a basal program specified by a user as described above in relation to FIGS. 2-8. The graphical portion can dynamically display a temporary adjustment made by a user to a predetermined basal program (e.g., a change to one or more basal rates over one or more time segments) as described in relation to FIGS. 9-13.

Figure 16:
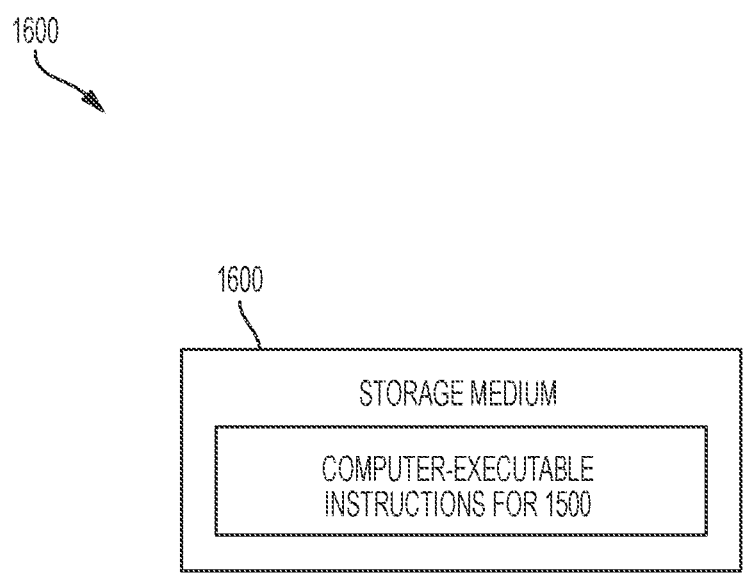
FIG. 16 illustrates an embodiment of a storage medium.

FIG. 16 illustrates an embodiment of a storage medium 1600. Storage medium 1600 may comprise any non-transitory computer-readable storage media or machine-readable storage media, such as an optical, magnetic or semiconductor storage media. In various embodiments, storage medium 1600 may comprise an article of manufacture. In some embodiments, storage medium 1600 may store computer-executable instructions, such as computer-executable instructions to implement logic flow 1500 of FIG. 15.

Examples of a computer-readable storage medium or machine-readable storage medium may include any tangible media capable of storing electronic data, including volatile memory or non-volatile memory, removable or non-removable memory, erasable or non-erasable memory, writeable or re-writeable memory, and so forth. Examples of computer-executable instructions may include any suitable type of code, such as source code, compiled code, interpreted code, executable code, static code, dynamic code, object-oriented code, visual code, and the like. The storage medium 1600 may include instructions to be executed by the processor 108 for implementing the user interfaces described herein. The embodiments are not limited in this context.

The user interfaces described herein and depicted in FIGS. 2-14 can include any textual and/or graphical depictions of a basal program including temporary modifications thereof. The user interfaces can use any coloring, shading, and diminished or muted contrast as part of any textual and/or graphical depictions. Further, the graphical portions of the user interfaces can be used for entry of information by a user by enabling a user to graphically manipulate graphical objects to vary input information. The user interfaces described herein are not limited to insulin related systems but can instead be applied to any user monitoring and/or drug delivery system.

The following examples pertain to additional embodiments:

Example 1 is a basal insulin management system comprising a processor operable with a memory and a display device, one or more input devices, an input signal receiver operable on the processor to receive one or more input signals from the one or more input devices, and a display controller operable on the processor to receive input information from the input signal receiver and to retrieve user interface information from the memory based upon the input information for the display of a user interface on the display device, the user interface including a first portion for textual display of user selected numerical values for a start time, an end time, and a basal rate for a first time segment of a basal insulin program, and a second portion for graphical display of the start time, the end time, and the basal rate on a timeline representing a duration of the basal insulin program, the start time graphically represented by a start bar along the timeline, the end time graphically represented by an end bar along the timeline, and the basal rate represented by a basal rate bar connecting the start bar and the end bar and having a size corresponding to the basal rate.

Example 2 is an extension of Example 1 or any other example disclosed herein, the basal insulin management system of claim 1, the display controller operable to adjust a position of the start bar along the timeline as the user changes the numerical value for the start time.

Example 3 is an extension of Example 1 or any other example disclosed herein, the display controller operable to adjust a position of the end bar along the timeline as the user changes the numerical value for the end time.

Example 4 is an extension of Example 1 or any other example disclosed herein, the display controller operable to adjust the size of the basal rate bar as the user changes the numerical value for the basal rate.

Example 5 is an extension of Example 1 or any other example disclosed herein, wherein the user interface comprises a confirmation input for the user to confirm the start time, the end time, and the basal rate for the first time segment.

Example 6 is an extension of Example 1 or any other example disclosed herein, wherein the second portion graphically displays user selected start times, end times, and basal rates for one or more additional time segments with the user selected start time, end time, and basal rate for the first time segment, the first time segment, the one or more additional time segments, and corresponding basal rates forming the basal insulin program.

Example 7 is an extension of Example 6 or any other example disclosed herein, a communications controller operable on the processor to transmit the basal insulin program to a remote drug delivery device.

Example 8 is an extension of Example 7 or any other example disclosed herein, the remote drug delivery device to implement the basal insulin program by delivering insulin to the user in accordance with the user selected basal rates for the corresponding user selected time segments.

Example 9 is a computer-implemented method for controlling a user interface of a basal insulin management system comprising receiving, by an input signal receiver operable on a processor, one or more input signals from one or more input devices, receiving, by a display controller operable on the processor, input information based upon the one or more input signals, displaying, by the display controller operable on the processor, a user interface on a display device, the user interface including a first portion for textually displaying user selected numerical values for a start time, an end time, and a basal rate for a first time segment of a basal insulin program and a second portion for graphically displaying the start time, the end time, and the basal rate on a timeline representing a duration of the basal insulin program, the start time graphically represented by a start bar along the timeline, the end time graphically represented by an end bar along the timeline, and the basal rate graphically represented by a basal rate bar connecting the start bar and the end bar and having a size corresponding to the basal rate, the display controller adjusting a position of the start bar based on user selected changes to the start time, adjusting a position of the end bar based on user selected changes to the end time, and adjusting the size of the basal rate bar based on user selected changes to the basal rate.

Example 10 is an extension of Example 9 or any other example disclosed herein, further comprising receiving a confirmation input from the user confirming the user selected start time, end time, and basal rate for the first time segment.

Example 11 is an extension of Example 9 or any other example disclosed herein, further comprising the second portion graphically displaying user selected start times, end times, and basal rates for at least one additional time segment with the user selected start time, end time, and basal rate for the first time segment, the first time segment, the at least one additional time segment, and corresponding basal rates for the first time segment and the at least one additional time segment forming the basal insulin program.

Example 12 is an extension of Example 11 or any other example disclosed herein, further comprising transmitting, by a communications controller operable on the processor, the basal insulin program to a remote drug delivery device.

Example 13 is an extension of Example 12 or any other example disclosed herein, further comprising implementing the basal insulin program by delivering insulin to the user with the remote drug delivery device in accordance with the user selected basal rates for the corresponding user selected time segments.

Example 14 is an article comprising a non-transitory computer-readable storage medium including instructions that, when executed by a processor, enable a basal insulin management system to receive, by an input signal receiver operable on a processor, one or more input signals from one or more input devices, receive, by a display controller operable on the processor, input information based upon the one or more input signals, display, by the display controller operable on the processor, a user interface on a display device, the user interface including a first portion for displaying user selected numerical values for a start time, an end time, and a basal rate for a first time segment of a basal insulin program, and a second portion for graphically representing the start time, the end time, and the basal rate on a timeline representing a duration of the basal insulin program, the start time graphically represented by a start bar along the timeline, the end time graphically represented by an end bar along the timeline, and the basal rate graphically represented by a basal rate bar connecting the start bar and the end bar and having a size corresponding to the basal rate, the display controller operable to adjust a position of the start bar based on user selected changes to the start time, adjust a position of the end bar based on user selected changes to the end time, and adjust the size of the basal rate bar based on user selected changes to the basal rate.

Example 15 is a method for generating a temporary adjustment to a portion of a basal insulin program comprising displaying on a touch-sensitive display a start time bar on a timeline graphically depicting a duration of the basal insulin program, the start time bar corresponding to a current time, selecting on the touch-sensitive display an end time of the temporary adjustment, displaying on the touch-sensitive display an end time bar corresponding to the selected end time on the timeline, selecting on the touch-sensitive display a temporary basal rate adjustment for a segment of time graphically depicted between the start time bar and the end time bar, and displaying on the touch-sensitive display a graphical representation of the selected temporary basal rate adjustment within the segment of time, the graphical representation of the selected temporary basal rate adjustment showing a difference between an initial basal rate of the basal insulin program and the selected temporary basal rate adjustment, the graphical representation of the selected temporary basal rate positioned between the start time bar and the end time bar.

Example 16 is an extension of Example 15 or any other example disclosed herein, further comprising dynamically displaying the end time bar on the touch sensitive display as a user changes possible values of the end time.

Example 17 is an extension of Example 15 or any other example disclosed herein, further comprising dynamically displaying the graphical representation of the selected temporary basal rate adjustment on the touch-sensitive display as a user changes possible values of the temporary basal rate adjustment.

Example 18 is an extension of Example 17 or any other example disclosed herein, further comprising displaying the initial basal rate as a dashed line for a decreased temporary basal rate adjustment.

Example 19 is an extension of Example 17 or any other example disclosed herein, further comprising displaying, for an increased temporary basal rate adjustment, the initial basal rate in a first color and the increased temporary basal rate adjustment on top of the initial basal rate in a second, different color.

Example 20 is an extension of Example 15 or any other example disclosed herein, further comprising transmitting an indication of the segment of time and the selected temporary basal rate to a remote drug delivery device.

Example 21 is a basal insulin management system comprising a processor operable with a memory and a display device, one or more input devices, an input signal receiver operable on the processor to receive one or more input signals from the one or more input devices, and a display controller operable on the processor to receive input information from the input signal receiver and to retrieve user interface information from the memory based upon the input information for the display of a user interface on the display device, the user interface including a first portion for displaying user selected numerical values for an end time of a temporary basal rate adjustment and a temporary basal rate adjustment for a portion of a basal insulin program, and a second portion for graphically representing a start time for the temporary basal rate adjustment, the end time, and the basal rate on a timeline representing a duration of the basal insulin program, the start time graphically represented by a start bar along the timeline and corresponding to a current time, the end time graphically represented by an end bar along the timeline, and the temporary basal rate adjustment graphically represented as a difference between an initial basal rate of the basal insulin program and the selected temporary basal rate adjustment for the selected portion of the basal insulin program.

Example 22 is an extension of Example 21 or any other example disclosed herein, wherein for a decreased temporary basal rate adjustment, the initial basal rate of the basal insulin program is displayed as a dashed line.

Example 23 is an extension of Example 21 or any other example disclosed herein, wherein for an increased temporary basal rate adjustment, the initial basal rate is displayed in a first color and the increased temporary basal rate adjustment is shown on top of the initial basal rate in a second, different color.

Example 24 is an extension of Example 21 or any other example disclosed herein, a communications controller operable on the processor to transmit the selected temporary basal rate adjustment and the selected portion of the basal insulin program to a remote drug delivery device.

The following examples pertain to further additional embodiments:

Example 1 is a method for generating a basal insulin program comprising (a) selecting on a touch-sensitive display an end time for a first time segment of the basal insulin program, (b) displaying on the touch-sensitive display an end time bar corresponding to the selected end time on a timeline graphically depicting a duration of the basal insulin program, (c) selecting on the touch-sensitive display a basal rate for the first time segment, (d) displaying on the touch-sensitive display a basal rate bar having a thickness corresponding to the selected basal rate, the basal rate bar positioned between a start time bar and the end time bar, and (e) repeating steps (a)-(d) for each time segment of the basal insulin program.

Example 2 is an extension of Example 1 or any other example disclosed herein, further comprising displaying on the touch-sensitive display each defined time segment and each corresponding basal rate graphically on the timeline.

Example 3 is an extension of Example 1 or any other example disclosed herein, wherein the end time bar is dynamically displayed on the touch-sensitive display as a user scrolls through possible values of the end time.

Example 4 is an extension of Example 1 or any other example disclosed herein, wherein the basal rate bar is dynamically displayed on the touch-sensitive display as a user scrolls through possible values of the basal rate.

Example 5 is an extension of Example 1 or any other example disclosed herein, further comprising displaying on the touch-sensitive display a start time bar corresponding to a default start time of the basal insulin program on the timeline.

Example 6 is an extension of Example 5 or any other example disclosed herein, further comprising, for a second time segment of the basal insulin program, displaying on the touch-sensitive display the start time bar adjacent to an end of the first time segment.

Example 7 is an extension of Example 6 or any other example disclosed herein, further comprising displaying on the touch-sensitive display a second basal rate bar representing a default basal rate for the second time segment that corresponds to the selected basal rate for the first time segment.

Example 8 is an extension of Example 7 or any other example disclosed herein, wherein the second basal rate bar representing the default basal rate is indicated by a first color and the basal rate bar representing the selected basal rate of the first time segment is indicated by a second, different color.

Example 9 is a method for generating a temporary adjustment to a portion of a basal insulin program comprising displaying on a touch-sensitive display a start time bar on a timeline graphically depicting a duration of the basal insulin program, the start time bar corresponding to a current time, selecting on the touch-sensitive display an end time of the temporary adjustment, displaying on the touch-sensitive display an end time bar corresponding to the selected end time on the timeline, selecting on the touch-sensitive display a temporary basal rate adjustment of a segment of time graphically depicted by a difference on the timeline between the start time bar and the end time bar, displaying on the touch-sensitive display a graphical representation of the selected temporary basal rate adjustment, the graphical representation of the selected temporary basal rate adjustment showing a difference between an initial basal rate of the basal insulin program and the selected temporary basal rate adjustment, the graphical representation of the selected temporary basal rate positioned between the start time bar and the end time bar.

Example 10 is an extension of Example 9 or any other example disclosed herein, wherein the end time bar is dynamically displayed on the touch-sensitive display as a user scrolls through possible values of the end time.

Example 11 is an extension of Example 9 or any other example disclosed herein, wherein the graphical representation of the selected temporary basal rate adjustment is dynamically displayed on the touch-sensitive display as a user scrolls through possible values of the temporary basal rate adjustment.

Example 12 is an extension of Example 11 or any other example disclosed herein, wherein for a decreased temporary basal rate adjustment, the initial basal rate of the basal insulin program is displayed as an outline.

Example 13 is an extension of Example 11 or any other example disclosed herein, wherein for an increased temporary basal rate adjustment, the initial basal rate of the basal insulin program is displayed in a first color and the increased temporary basal rate adjustment is shown on top of the initial basal rate of the basal insulin program in a second, different color.

Example 14 is an apparatus comprising a processor operable with a memory and a display device, one or more input devices, an input signal receiver operable on the processor to receive one or more input signals from the one or more input devices, and a display controller operable on the processor to receive input information from the input signal receiver and to retrieve user interface information from the memory based upon the input information for the display of a user interface on the display device, the user interface including a first portion for textually displaying user selected values for a basal insulin program comprising one or more time segments and corresponding basal insulin rates and a second portion graphically displaying the one or more time segments and corresponding basal insulin rates.

Example 15 is an extension of Example 14 or any other example disclosed herein, wherein the display device is a touchscreen.

Example 16 is an extension of Example 15 or any other example disclosed herein, wherein the one or more time segments and corresponding basal insulin rates are dynamically displayed in the second portion as the user manipulates possible time segment values and corresponding basal rate values.

Example 17 is a portable electronic device comprising a touch-sensitive display, a memory, one or more processors and one or more modules stored in the memory and configured for execution by the one or more processors, the one or more modules including instructions to receive an end time for a first time segment of a basal insulin program, the end time selected by a user by manipulating the touch-sensitive display, to display on the touch-sensitive display an end time bar corresponding to the user-selected end time on a timeline graphically depicting the basal insulin program, to receive a basal rate for the first time segment, the basal rate selected by the user manipulating the touch-sensitive display, and to display on the touch-sensitive display a rate bar corresponding to the user-selected basal rate on the timeline between a start time and the selected end time.

Example 18 is at least one computer-readable storage medium for use in conjunction with a portable electronic computing device comprising a touch-sensitive display, the computer-readable storage medium comprising a set instructions that, in response to being executed on the portable electronic computing device, cause the portable electronic computing device to receive an end time for a first time segment of a basal insulin program, the end time selected by a user by manipulating the touch-sensitive display, display on the touch-sensitive display an end time bar corresponding to the user-selected end time on a timeline graphically depicting the basal insulin program, receive a basal rate for the first time segment, the basal rate selected by the user manipulating the touch-sensitive display, and display on the touch-sensitive display a rate bar on the timeline corresponding to the user-selected basal rate between a start time and the selected end time.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

The invention claimed is:

1. A device, comprising:
    a display device;
    an input device;
    a memory storing computer-executable instructions; and
    a processor coupled to the display device, the input device, and the memory, the processor operable to execute the computer-executable instructions, wherein, when the processor is executing the computer-executable instructions, the processor is operable to:
    receive, via the input device, a numerical value for a temporary basal rate adjustment and a numerical value for a duration of the temporary basal adjustment rate;
    determine, based on a current time and the numerical value for the duration of the temporary basal rate adjustment, a portion of a basal insulin program during which a temporary basal rate adjustment is to be administered;
    determine a temporary basal rate adjustment for a first time segment of a basal insulin program based on a difference between a basal rate and the temporary basal rate adjustment;
    determine a numerical value of a new basal rate for the first time segment based on the basal rate and the temporary basal rate adjustment; and
    present a user interface on the display device, the user interface including:
        a first portion configured to display the numerical value for the duration of the temporary basal rate adjustment and a numerical value for the temporary basal rate adjustment for the determined portion of the basal insulin program, wherein the determined portion of the basal insulin program overlaps the first time segment of the basal insulin program, and
        a second portion configured to graphically represent the temporary basal rate adjustment for the first time segment with the numerical value of the new basal rate for the first time segment is further displayed.

2. The device of claim 1, wherein the processor is further operable to:
    receive, via the input device, an input of a numerical value of a start time for the first time segment of the basal insulin program;
    receive, via the input device, an input of a numerical value of an end time for the first time segment of the basal insulin program;
    receive, via the input device, an input of a numerical value of a basal rate for the first time segment of the basal insulin program; and
    adjust, via a display controller operable on the processor, a position of a start bar along a timeline in response to the received input of the numerical value of the start time.

3. The device of claim 2, wherein the processor via the display controller operable the processor is operable to:
    adjust a position of an end bar along the timeline in response to the received input of the numerical value of the end time.

4. The device of claim 2, wherein the processor via the display controller operable the processor is operable to:
    adjust a size of a basal rate bar as a user changes the numerical value for the basal rate.

5. The device of claim 2, wherein the user interface comprises a confirmation input for confirmation of the numerical value for the start time, the numerical value for the end time, and the numerical value for the basal rate for the first time segment.

6. The device of claim 1, wherein the second portion further graphically displays the first time segment, one or more additional time segments, and basal rates corresponding to the first time segment and the one or more additional time segments forming the basal insulin program.

7. The device of claim 6, further comprising:
    a communications controller operable on the processor to transmit the basal insulin program to a remote drug delivery device.

8. The device of claim 1, wherein the processor, when presenting the user interface, is further operable to:
    present, in the first portion, a textual display of user selected numerical values for a start time, an end time, and a basal rate for a first time segment of a basal insulin program.

9. The device of claim 1, wherein the processor, when presenting the user interface, is further operable to:
    present, in the second portion, a graphical display of user selected numerical values for a start time, an end time, and a basal rate on a timeline representing a duration of the basal insulin program.

10. The device of claim 9, wherein the processor, when presenting the graphical display in the second portion, is further operable to graphically represent:
    the start time using a start bar along the timeline,
    the end time using an end bar along the timeline, and
    the basal rate using a basal rate bar connecting the start bar and the end bar.

11. A non-transitory computer-readable storage medium embodied with programming instructions that, when executed by a processor, enable the processor to:
    receive a numerical value for a temporary basal rate adjustment and a numerical value for a duration of the temporary basal adjustment rate;
    determine, based on a current time and the numerical value for the duration of the temporary basal rate adjustment, a portion of a basal insulin program during which a temporary basal rate adjustment is to be administered;
    determine a temporary basal rate adjustment for a first time segment of a basal insulin program based on a difference between a basal rate and the temporary basal rate adjustment;
    determine a numerical value of a new basal rate for the first time segment based on the basal rate and the temporary basal rate adjustment; and
    enable display of a user interface on a display device, the user interface having:

a first portion configured to display the numerical value for the duration of the temporary basal rate adjustment and a numerical value for the temporary basal rate adjustment for the determined portion of the basal insulin program, wherein the determined portion of the basal insulin program overlaps the first time segment of the basal insulin program, and a second portion configured to graphically represent the temporary basal rate adjustment for the first time segment with the numerical value of the new basal rate for the first time segment is further displayed.

12. The non-transitory computer-readable storage medium of claim 11, embodied with further programming instructions that, when executed by a processor, enable the processor to:

receive a numerical value of a start time for the first time segment of the basal insulin program;

receive a numerical value of an end time for the first time segment of the basal insulin program;

receive a numerical value of a basal rate for the first time segment of the basal insulin program; and cause an adjustment of a position of a start bar along a timeline in response to the received numerical value of the start time.

13. The non-transitory computer-readable storage medium of claim 12, embodied with further programming instructions that, when executed by a processor, enable the processor to:

adjust a position of an end bar along the timeline in response to the received numerical value of the end time.

14. The non-transitory computer-readable storage medium of claim 12, embodied with further programming instructions that, when executed by a processor, enable the processor to:

adjust a size of a basal rate bar as the numerical value for the basal rate is changed.

15. The non-transitory computer-readable storage medium of claim 12, embodied with further programming instructions that, when executed by a processor, enable the processor to:

receive a confirmation input confirming the numerical value of the start time, the numerical value of the end time, and the numerical value of the basal rate for the first time segment.

16. The non-transitory computer-readable storage medium of claim 15, embodied with further programming instructions that, when executed by a processor, enable the processor to:

cause display of a rate bar on the timeline corresponding to the confirmed numerical value of the basal rate for the first time segment between the confirmed numerical value of the start time and the confirmed numerical value of the end time.

17. The non-transitory computer-readable storage medium of claim 11, embodied with further programming instructions that, when executed by a processor, enable the processor to:

cause display of the first time segment, one or more additional time segments, and basal rates corresponding to the first time segment and the one or more additional time segments forming the basal insulin program.

18. The non-transitory computer-readable storage medium of claim 11, embodied with further programming instructions that, when executed by a processor, enable the processor to:

cause presentation, in the first portion, of a textual display of user selected numerical values for a start time, an end time, and a basal rate for a first time segment of a basal insulin program.

19. The non-transitory computer-readable storage medium of claim 11, embodied with further programming instructions that, when executed by a processor, enable the processor to:

cause presentation, in the second portion, of a graphical display of user selected numerical values for a start time, an end time, and a basal rate on a timeline representing a duration of the basal insulin program.

20. The non-transitory computer-readable storage medium of claim 19, embodied with further programming instructions that, when executed by a processor, enable the processor, when causing the display in the second portion to further cause the representation of:

the numerical value of the start time as a start bar along the timeline, the numerical value of the end time as an end bar along the timeline, and the numerical value of the basal rate as a basal rate bar connecting the start bar and the end bar and having a size corresponding to the basal rate.

* * * * *